(12) United States Patent
Williamson et al.

(10) Patent No.: US 7,531,095 B2
(45) Date of Patent: May 12, 2009

(54) SYSTEM FOR PREDICTING REDUCTION IN CONCENTRATION OF A TARGET MATERIAL IN A FLOW OF FLUID

(75) Inventors: Christian Williamson, Tucson, AZ (US); Alan Royce, London (CA); Mihaela I. Stefan, London (CA)

(73) Assignee: Trojan Technologies Inc. (CA)

( * ) Notice: Subject to any disclaimer, the term of this patent is extended or adjusted under 35 U.S.C. 154(b) by 391 days.

(21) Appl. No.: 11/076,426

(22) Filed: Mar. 10, 2005

(65) Prior Publication Data

US 2005/0218082 A1    Oct. 6, 2005

Related U.S. Application Data

(60) Provisional application No. 60/551,350, filed on Mar. 10, 2004.

(51) Int. Cl.
  *C02F 1/32*    (2006.01)
  *C02F 1/42*    (2006.01)
(52) U.S. Cl. ........................ 210/739; 210/748
(58) Field of Classification Search ........ 210/748, 210/198.1, 188; 250/474.1
  See application file for complete search history.

(56) References Cited

U.S. PATENT DOCUMENTS

| | | | | |
|---|---|---|---|---|
| 5,028,792 A | * | 7/1991 | Mullis | 250/474.1 |
| 6,264,836 B1 | * | 7/2001 | Lantis | 210/188 |
| 6,541,777 B1 | | 4/2003 | Lombardo et al. | |
| 6,733,661 B2 | * | 5/2004 | Mukogawa et al. | 210/93 |
| 2004/0045886 A1 | * | 3/2004 | Abe et al. | 210/198.1 |

FOREIGN PATENT DOCUMENTS

| | | |
|---|---|---|
| CA | 2345423 A1 | 4/2000 |
| CA | 2395801 A1 | 4/2001 |
| CA | 2473540 A1 | 7/2003 |
| WO | 03/024874 A2 | 3/2003 |
| WO | 03/072508 A2 | 9/2003 |

OTHER PUBLICATIONS

International Search Report for International Application No. PCT/CA2005/000363.

* cited by examiner

*Primary Examiner*—Walter D Griffin
*Assistant Examiner*—Cameron J Allen
(74) *Attorney, Agent, or Firm*—Katten Muchin Rosenman LLP

(57) ABSTRACT

An ultraviolet fluid treatment system having feedback control using a kinetic model and a reactor model that interact with one another. The kinetic model uses readily measured fluid properties upstream and downstream of a radiation zone to calculate the conversion of a target contaminant as it passes through the fluid treatment system. This obviates the need to measure the contaminant concentration directly, which generally is too slow to permit real-time control. A reactor model relates system operating cost to system operating parameters, such as electrical power consumption and/or rate of oxidant addition, where applicable. The reactor model is linked to the kinetic model and is used to optimize operating cost by adjusting system operating parameters based on a comparison between the conversion obtained from the kinetic model and the overall treatment objectives. A control center, an ultraviolet fluid treatment apparatus, and a method of treating a fluid are also disclosed.

47 Claims, 10 Drawing Sheets

SYSTEM FOR PREDICTING REDUCTION IN CONCENTRATION OF A TARGET MATERIAL IN A FLOW OF FLUID

CROSS-REFERENCE TO RELATED APPLICATION

The present application claims the benefit under 35 U.S.C. §119(e) of provisional patent application Ser. No. 60/551,350, filed Mar. 10, 2004, the contents of which are hereby incorporated by reference.

BACKGROUND OF THE INVENTION

1. Field of the Invention

The invention relates to a radiation (e.g., ultraviolet radiation) fluid treatment systems and to a method for radiation (e.g., ultraviolet radiation) treatment of a fluid. More particularly, in a preferred embodiment, the invention relates to a treatment system which is controllable using both a kinetic model and a reactor model that interact with one another.

2. Description of the Prior Art

Ultraviolet fluid treatment systems are used, for example, in the disinfection or other treatment of fluids contaminated with microorganisms and in the oxidation and degradation of chemical contaminants. A variety of ultraviolet fluid treatment devices are used in these systems. See, for example, U.S. Pat. No. 4,872,980, U.S. Pat. No. Re 36,896, U.S. Pat. No. 6,500,346, International Publication Number WO 03/024,874 and International Publication Number WO 03/072,508, all of which are assigned to the assignee of the present invention. Each of these devices has a radiation zone in which the fluid is exposed to radiation (e.g., ultraviolet radiation) supplied by one or more radiation (e.g., ultraviolet) sources or lamps immersed in the fluid being treated.

There is an ongoing need to reduce or minimize the operating cost of radiation treatment systems such as ultraviolet fluid treatment systems. One of the operating costs is the electrical energy used to power the ultraviolet lamps. In some systems, especially those used in the oxidation of chemical contaminants, an oxidant, for example hydrogen peroxide and/or ozone, is added to the fluid prior to irradiation and is consumed during fluid treatment. The consumption of oxidant is another operating cost of these systems. Controlling the amount of electrical energy and, where applicable, the amount of oxidant used is important in reducing the overall operating costs of an ultraviolet fluid treatment system.

Various means of controlling ultraviolet fluid treatment systems have been proposed. Typically, these means do not use feedback control to optimize system operating parameters based on a comparison of fluid treatment system performance versus the treatment objectives. Usually, control is based only on a measurement of a single set of fluid properties, such as the transmittance of the fluid to ultraviolet light, the fluid flow rate, etc., and the measurement is typically made only upstream of the ultraviolet radiation zone. On rare occasions where feedback control has been used and measurements have been taken both upstream and downstream of the radiation zone, the time required for analysis of actual target contaminant concentration is typically too long to be practical for real-time control of the fluid treatment system operating parameters. In addition, a reactor model relating system operating cost to electrical energy consumption and, where applicable, oxidant consumption has not been previously employed for ultraviolet fluid treatment system control. Although kinetic models have been used to predict contaminant conversion, these models are based on measurements of the actual target contaminant concentration, not on more readily measured fluid properties that may be used to approximate system performance, and have not been linked with a reactor model to optimize system operating cost through control of system parameters.

U.S. Pat. No. 5,151,252 [Mass] discloses that the concentration of material in the fluid treatment chamber can be calculated from first order kinetics for photochemical reactions and that the fluid flow rate and/or lamp output may be adjusted as a function of concentration—see column 6, lines 2-20. No description is provided of a practical control system in which a kinetic model is used with a reactor model to control an ultraviolet fluid treatment system. Also, when using the Mass approach, the concentration of the contaminant must be measured. Measurement of contaminants typically cannot be completed rapidly enough to be useful in controlling the amount of electrical energy or oxidant supplied to the fluid treatment system on a real-time basis.

U.S. Pat. No. 6,023,065 [Garver, Jr.] discloses a method and apparatus for monitoring and controlling hydrogen peroxide and ozone concentrations in pulp and paper bleaching. The method and apparatus make use of ultraviolet light as a measurement tool for computing an empirical value of a characteristic of the effluent. The apparatus does not make use of ultraviolet light as part of a fluid treatment system and relies on a single empirical model for feedback control.

U.S. Pat. No. 6,269,680 [Prieve et al.] discloses a sterilization chamber using hydrogen peroxide in the vapour phase. Ultraviolet light is used as a measurement tool in assessing the concentration of hydrogen peroxide, which is used as a parameter in a feedback control system for a hydrogen peroxide dosing pump. Ultraviolet light is not used as part of a fluid treatment system and the controlled variable, hydrogen peroxide concentration, is measured directly, obviating the need for a kinetic model to determine the concentration.

The need therefore exists for improvements in the control of radiation fluid treatment systems such as ultraviolet fluid treatment systems.

SUMMARY OF THE INVENTION

It is an object of the present invention to obviate or mitigate at least one of the above-mentioned disadvantages of the prior art.

Accordingly, in one of its aspects, the present invention provides an ultraviolet fluid treatment system for treating a fluid containing a contaminant, the system comprising: a fluid inlet, a fluid outlet, and an ultraviolet radiation zone between the fluid inlet and the fluid outlet; an upstream measurement point for use in measuring a first set of fluid properties upstream of the radiation zone; a downstream measurement point for use in measuring a second set of fluid properties downstream of the radiation zone; a controller for adjusting one or more system parameters and for providing values of the one or more system parameters; and, a programmable logic device for calculating a conversion of the contaminant using a kinetic model and for calculating an adjustment to the one or more system parameters using a reactor model employing the conversion, the programmable logic device in communication with the controller.

In another of its aspects, the present invention provides a control center for an ultraviolet fluid treatment system for treating a fluid containing a contaminant, the control center comprising:

a controller for adjusting one or more system parameters and for providing values of the one or more system parameters; and, a programmable logic device for calculating a conversion of the contaminant using a kinetic model and for calculating an adjustment to the one or more system parameters using a reactor model employing the conversion, the programmable logic device in communication with the controller.

In yet another of its aspects, the present invention provides an ultraviolet fluid treatment system for treating a fluid containing a contaminant, the system comprising:

a fluid inlet, a fluid outlet, an ultraviolet radiation zone between the fluid inlet and the fluid outlet, and an oxidant injection site upstream of the radiation zone for injecting an oxidant into the fluid;

an upstream measurement point for use in measuring a first set of fluid properties upstream of the radiation zone, the first set of fluid properties including a first concentration of the oxidant;

a downstream measurement point for use in measuring a second set of fluid properties downstream of the radiation zone, the second set of fluid properties including a second concentration of the oxidant;

a controller for adjusting one or more system parameters and for providing values of the one or more system parameters; and, a programmable logic device for calculating a conversion of the contaminant using a kinetic model employing the difference between the first concentration of oxidant and the second concentration of oxidant and for calculating an adjustment to the one or more system parameters using a reactor model employing the conversion, the programmable logic device in communication with the controller.

In yet another of its aspects, the present invention provides a method of treating a fluid using ultraviolet radiation, the fluid containing a contaminant, the method comprising:

measuring a first set of fluid properties; followed by, exposing the fluid to ultraviolet radiation having an intensity; followed by, measuring a second set of fluid properties;

calculating a conversion of the contaminant using a kinetic model;

calculating a difference between the conversion and a target;

calculating an adjustment to the intensity, the first set of fluid properties, or any combination thereof in order to reduce the difference, the adjustment calculated using a reactor model including the conversion, the target, the intensity, and one of the first set of fluid properties, the second set of fluid properties or the first and second sets of fluid properties; and, implementing the adjustment to the intensity, the first set of fluid properties, or any combination thereof.

In yet another of its aspects, the present invention provides a system for predicting the reduction in concentration of a target material to a predetermined concentration in a flow of fluid passing through a fluid treatment zone in a fluid treatment device, the flow of fluid comprising a marker compound, the system comprising:

(i) a first measurement device to obtain a first measurement comprising the concentration of the marker compound in the flow of fluid at a first location and a second measurement device to obtain a second measurement comprising the concentration of the marker compound in the flow of fluid at a second location, the second location being downstream with respect to the first location, (ii) means to correlate the first measurement and the second measurement to a calculated concentration of the target material, (iii) means to compare the calculated concentration with the predetermined concentration; and (iv) means to adjust at least one process parameter if the calculated concentration different than the predetermined concentration.

In yet another of its aspects, the present invention provides a method for predicting the reduction in concentration of a target material to a predetermined concentration in a flow of fluid passing through a fluid treatment zone in a fluid treatment device, the flow of fluid comprising a marker compound, the method comprising the steps of:

(i) obtaining a first measurement comprising the concentration of the marker compound in the flow of fluid at a first location (ii) obtaining a second measurement comprising the concentration of the marker compound in the flow of fluid at a second location, the second location being downstream with respect to the first location, (iii) correlating the first measurement and the second measurement to a calculated concentration of the target material, (iv) comparing the calculated concentration with the predetermined concentration; and (v) adjusting at least one process parameter if the calculated concentration is different than the predetermined concentration In yet another of its aspects, the present invention provides a system for predicting the reduction in concentration of a target contaminant to a predetermined concentration in a flow of water passing through an ultraviolet radiation treatment zone comprising an array of ultraviolet radiation sources, the flow of water comprising an oxidant, the system comprising:

(i) a first measurement device to obtain a first concentration of the oxidant in the flow of water at a first location and a second measurement device to obtain a second concentration of the oxidant in the flow of water at a second location, the second location being downstream with respect to the first location, (ii) means to correlate the first concentration and the second concentration to a calculated concentration of the target contaminant, (iii) means to compare the calculated concentration with the predetermined concentration; and (iv) means to adjust at least one process parameter if the calculated concentration different than the predetermined concentration.

In yet another of its aspects, the present invention provides a method for predicting the reduction in concentration of a target contaminant to a predetermined concentration in a flow of water passing through an ultraviolet radiation treatment zone comprising an array of ultraviolet radiation sources, the flow of water comprising an oxidant, the method comprising the steps of:

(i) obtaining a first concentration of the oxidant in the flow of water at a first location;

(ii) obtaining a second concentration of the oxidant in the flow of water at a second location, the second location being downstream with respect to the first location, (iii) correlating the first concentration and the second concentration to a calculated concentration of the target contaminant, (iv) comparing the calculated concentration with the predetermined concentration of the target contaminant; and (v) adjusting at least one process parameter if the calculated concentration is different than the predetermined concentration.

The invention provides an ultraviolet fluid treatment system having feedback control using a kinetic model and a reactor model that interact with one another. The kinetic model uses readily measured fluid properties upstream and downstream of a radiation zone to calculate conversion of a target contaminant as it passes through the fluid treatment system. This obviates the need to measure the contaminant concentration directly, which generally is too slow to permit real-time control. A reactor model relates system operating cost to system operating parameters, such as electrical power consumption and/or rate of oxidant addition, where applicable. The reactor model is linked to the kinetic model and is used to optimize operating cost by adjusting system operating parameters based on a comparison between the conversion obtained from the kinetic model and the overall treatment objectives.

The contaminated fluid may comprise a gas or a liquid. A variety of contaminated fluids may be treated (for example: air; water, such as wastewater, drinking water, groundwater, or re-use water; organic fluids, etc.). The contaminant present in the fluid may comprise one or more micro-organisms, one or more chemical compounds, or a combination thereof. Micro-organisms may comprise, for example, bacteria, viruses, fungi, protozoa, pathogens and the like, and may be treated by irradiation of the fluid with ultraviolet light of a germicidally active wavelength. Contaminated fluids containing chemical compounds may be treated by a variety of methods; for example: by direct photolysis with ultraviolet light of a specified wavelength or wavelengths; by oxidation in the presence of a photo-active oxidant that is added to the fluid; by oxidation in the presence of a photo-active catalyst that is in contact with the fluid; other treatment means to generate in-situ oxidants, such as ionizing radiation, ultrasonic, electrical, electrochemical means and the like; or, a combination thereof. Chemical compounds that may be treated by photolysis or photo-oxidation may comprise, for example: aromatic hydrocarbons (such as benzene, toluene, ethyl-benzene and xylene, commonly known as BTEX compounds); halogenated hydrocarbons (such as chlorinated BTEX compounds); ethers (such as methyl tert-butyl ether, commonly known as MTBE); nitrogen containing organic compounds (such as RDX, and amines, such as n-nitroso di-methyl amine, commonly known as NDMA); pesticides (such as atrazine); hormones; bio-toxins; taste and odour compounds (such as geosmin), arsenic, cyanide, etc.

Photo-active oxidants may comprise oxidants that dissociate to form oxidizing radicals, for example hydroxyl radicals (.OH), upon irradiation with ultraviolet light of a specified wavelength or wavelengths. Suitable oxidants may comprise, for example, hydrogen peroxide ($H_2O_2$), ozone ($O_3$), or a combination thereof. Oxidants may be added directly to the fluid to be treated and are consumed during fluid treatment as oxidizing radicals are formed. The oxidizing radicals are consumed by reaction with the contaminants, other oxidants, and background species present in the fluid that scavenge the oxidizing radicals.

Photo-active catalysts may comprise catalysts that form oxidizing radicals, for example hydroxyl radicals (.OH), when irradiated with ultraviolet light of a specified wavelength or plurality of wavelengths in the presence of water or water vapour. Suitable catalysts may comprise, for example, titanium dioxide ($TiO_2$), preferably in its anatase form. Catalysts may be provided on an inert support structure that permits recovery of the catalyst from the fluid being treated. Catalysts may be provided on an immobilized support, for example a porous structure within the radiation zone or an irradiated surface of the fluid treatment device. Alternatively, catalysts may be provided on a mobile support, such as a packing material that may be removably placed within the radiation zone. The design of fluid treatment systems incorporating photo-active catalysts is known to persons skilled in the art. Catalysts of any type may be used either alone or in conjunction with oxidants as part of an ultraviolet fluid treatment system.

An ultraviolet fluid treatment system may comprise an ultraviolet fluid treatment device. These devices typically comprise a fluid inlet, a fluid outlet, and a radiation zone between the fluid inlet and the fluid outlet. Treatment of the fluid may take place in either an enclosed vessel or an open channel ultraviolet fluid treatment device. For example, when the fluid being treated is drinking water or the like, the fluid inlet, the fluid outlet, and the radiation zone are preferably enclosed; whereas, when the fluid being treated is wastewater, the fluid inlet, fluid outlet, and/or radiation zone may be either open to atmosphere or enclosed. The radiation is provided by an ultraviolet radiation source, for example, one or more ultraviolet lamps. Ultraviolet lamps may be immersed in the fluid and may be contained within a protective sleeve or envelope made from a material transparent to the wavelength or wavelengths of ultraviolet light emitted by the lamp, for example, a quartz material. Alternatively, the ultraviolet radiation source may be remote from the fluid, for example, positioned above the fluid or around the periphery of the radiation zone.

An ultraviolet fluid treatment system may also comprise means for the addition of an oxidant to the fluid; for example, an oxidant metering device in fluid communication with an oxidant injector. The oxidant is added at one or more oxidant injection sites located upstream of the radiation zone and/or within the radiation zone. An oxidant injection site may be located within the ultraviolet fluid treatment device (for example, in the fluid inlet) or upstream of the device in the fluid conduits leading to the fluid inlet. There may be a plurality of oxidant injection sites that may be spaced apart along a flow path of the fluid treatment system. The oxidant may be in the liquid or gaseous phase. The oxidant may be generated on-site and may form part of the ultraviolet fluid treatment system. The fluid treatment system may incorporate means to promote fluid mixing to increase the uniformity of oxidant concentration within the fluid.

The ultraviolet fluid treatment system may also comprise upstream and downstream measurement points for use, respectively, in measuring a first and second set of fluid properties. The measurement points may be located within the ultraviolet fluid treatment device, or upstream and/or downstream of the device in the fluid conduits leading to the fluid inlet or from the fluid outlet, respectively. There may be a plurality of measurement points in the upstream and/or downstream locations. The plurality of measurement points may be spaced apart along a flow path of the fluid treatment system. The number of measurement points may correspond to the number of fluid properties being measured in a given set of fluid properties.

The first and second sets may contain different numbers of fluid properties. Either the first or second sets may comprise one fluid property. Fluid properties may be either physical or chemical properties of the fluid. Fluid properties may comprise, for example: rate of fluid flow; ultraviolet and/or visible light absorbance or transmittance by the fluid at a specified wavelength or wavelengths; turbidity; pH; conductivity; alkalinity; total organic carbon (TOC) concentration; concentration of chlorination agents; chemical oxygen demand (COD); biological oxygen demand (BOD); oxidation reduction potential (ORP); concentration of an oxidant; concentration of an actinometer; concentration of solids; temperature; or, any combination thereof. Persons skilled in the art will recognize that absorbance and transmittance are mathematically related and may be used interchangeably herein in the conveyance of concept. In the treatment of fluids containing chemical contaminants by oxidation, the first and second sets of fluid properties may comprise the concentration of an oxidant (for example, hydrogen peroxide, ozone, or a combination thereof). In the treatment of fluids containing chemical contaminants by photolysis, the first and second sets of fluid properties may comprise the concentration of an actinometer (for example: uridine; hydrogen peroxide; potassium ferrioxalate; potassium iodide/iodate; or, a combination thereof).

The degree of treatment of a contaminated fluid as it passes through the ultraviolet fluid treatment system may be expressed as a conversion. Conversion is calculated by taking the difference between the concentration of a contaminant at the fluid inlet ($C_i$) and the concentration of the contaminant at the fluid outlet ($C_o$) and dividing it by the concentration of the contaminant at the fluid inlet, expressed mathematically as $(C_i-C_o)/C_i$. The conversion may be expressed as a percentage or as an order of magnitude of conversion expressed as log $(C_i/C_o)$.

A fluid treatment system may have a given target conversion for each contaminant in the fluid and there may be a plurality of contaminants within a given fluid to be treated. One primary contaminant and its associated target conversion will be the controlling contaminant for which the operation of the UV fluid treatment system is to be optimized. The target conversion of each contaminant can be varied with time either through manual input or by a predefined function programmed into the programmable logic device. The nature of this variation of the target conversion(s) may include the case in which the primary contaminant, for which the system is controlled, switches from one contaminant to another. By means of example only, a UV fluid treatment system is envisioned for which the treatment of a chemical contaminant occurs by the combined application of UV and added oxidant and the simultaneous treatment of a microbiological contaminant occurs by UV photolysis only as well as by the combined process. Furthermore, the control of this UV fluid treatment system may switch between treatment of the chemical contaminant requiring the combined treatment and treatment of the microbiological contaminant requiring UV only. It is to be recognized that various means for control of UV fluid treatment systems for microbiological contaminants are described in the prior art (e.g., Dosimeter Patent). The control of the UV fluid treatment system may switch between the feedback control described in this application and control schemes described in the prior art. This discontinuity in the control of the UV fluid treatment system comprises a subset of this invention.

A number of system parameters may be adjusted to influence the conversion. For example, when the system comprises one or more ultraviolet lamps for providing ultraviolet radiation to the radiation zone, the system parameters may comprise power incident to the system, a power setting of the system, rate of fluid flow through the system, rate of addition of an oxidant to the system, or any combination thereof. Where the ultraviolet fluid treatment system comprises the addition of an oxidant, the system parameters preferably comprise the rate of addition of the oxidant.

A ballast is used to power one or more ultraviolet lamps; for example, a ballast may be used to power two lamps. The power incident to the system may comprise the input power delivered to the ballast. The power setting of the system may be a power setting of the ballast. The input power to the ballast and power setting of the ballast may be used to calculate the power delivered to the ultraviolet lamp or lamps connected to the ballast. The power delivered to the ultraviolet lamp or lamps may be a function of ballast power setting, ballast age, ballast power factor, or a combination thereof. The amount of ultraviolet radiation emitted from each lamp into the fluid may be measured or calculated and may be a function of the power delivered to the lamp, lamp temperature, lamp age, lamp type, lamp current, the degree of sleeve fouling or a combination thereof.

Ultraviolet radiation may be measured using an ultraviolet sensor. One or more ultraviolet sensors may be located within the radiation zone. The ultraviolet sensors may be used to measure the actual radiation intensity at a point within the radiation zone. The lamp output and resulting radiation intensity may be calculated theoretically and the degree of sleeve fouling deduced by comparing the theoretical intensity values with the measured intensity values. The degree of sleeve fouling may be expressed as a fouling factor. The ultraviolet sensor may be a broadband sensor for sensing a plurality of wavelengths. The ultraviolet sensor may be in communication with a system control center.

A control center may include means for receiving the first set of fluid properties, the second set of fluid properties, and/or additional input signals. The additional input signals may comprise measured parameters not related to the fluid; for example, the additional input signals may comprise an intensity measurement taken using an ultraviolet sensor. The control center may comprise an operator interface for displaying values of the first set of fluid properties, the second set of fluid properties, and/or the additional input signals. The control center may further comprise a controller and/or a programmable logic device.

A controller may be used to adjust one or more system parameters. The controller may be an electronic device in communication with, for example: a ballast or ballasts; a device for supplying power to the ballast or ballasts; a flow control device; a device used for supplying oxidant to the system; or, any combination thereof. The controller may be a commercially available electronic device that communicates with the various parts of the system using known communication protocols and pathways. The communication is preferably bi-directional so that the controller is also able to determine values of the one or more system parameters. The controller may form part of a system control center and may be in communication with an operator interface. The operator interface may be used for displaying the values of the one or more system parameters and for manually adjusting one or more system parameters using the controller.

The controller is in communication with a programmable logic device. The programmable logic device may be used to calculate a conversion of the one or more contaminants using a kinetic model that is programmed into the programmable logic device. The programmable logic device may also be used for calculating an adjustment to the one or more system parameters using a reactor model employing the conversion. The programmable logic device then communicates the adjustment to the controller, which adjusts the system parameters accordingly. The programmable logic device may form part of a system control center and may be located in an enclosure along with the controller. Alternatively, the programmable logic device could be located remotely from the controller, for example in a computer workstation that is in communication with the controller. The programmable logic device may be in communication with any number of controllers that are needed to adjust the desired system parameters.

The programmable logic device and controller may be co-located. For example, the functions of both the programmable logic device and the controller may be performed by a single electronic device, such as a programmable logic controller (PLC). The PLC may be a commercially available unit that is programmed to perform the functions of both the programmable logic device and the controller. The communication between the programmable logic device and the controller is then internal to the PLC.

The kinetic model employs the first and second sets of fluid properties to calculate a conversion of the one or more contaminants as the fluid being treated passes through the fluid treatment system. The kinetic model may employ first-order kinetic rate expressions relating the rate of contaminant conversion to the difference in the first and second sets of fluid properties. The kinetic model preferably uses one or more readily measured fluid properties to calculate conversion of the target contaminant; this advantageously obviates the need for measuring the concentration of the contaminant directly, as the analysis of contaminant concentration is typically not available quickly enough to be practical for real-time control of system parameters. A species added to the fluid may be measured and used as an analog for the difference in contaminant concentration. For example, when oxidation of a chemical contaminant using hydrogen peroxide is conducted, the kinetic model may employ the difference in upstream and downstream hydrogen peroxide concentrations, as obtained from the first and second sets of fluid properties to determine the average reactor concentration of hydroxyl radical (.OH) in the radiation zone and the first order kinetic rate expression for contaminant oxidation with .OH to calculate the approximate contaminant conversion through the system. Alternatively, for example in direct irradiation of a contaminant without an oxidant, a readily measured actinometer species having known photo-chemistry under irradiation by wavelengths present in the radiation zone may be present in or added to the fluid and a difference in measurements upstream and downstream of the radiation zone may be used with a kinetic rate expression to calculate contaminant conversion through the system. The actinometer species may comprise, for example, uridine, hydrogen peroxide, or potassium iodide/potassium iodate.

The kinetic model may include two or more pre-determined kinetic constants. One of the constants may be the rate constant for the reaction of a contaminant with another species, for example, .OH radicals. The kinetic model may include a background term that accounts for, for example, the scavenging of oxidizing radicals by other species present in the fluid. The background term may comprise another of the pre-determined kinetic constants. The pre-determined kinetic constants may be derived experimentally on a site-specific basis.

The contaminant conversion calculated using the kinetic model is provided to a reactor model. The reactor model relates the system operating cost, the system parameters, and the conversion. The reactor model may be used to determine an adjustment to one or more system parameters in order that the conversion approaches a pre-determined target value. The reactor model may employ the conversion, the target value, an intensity of radiation within the radiation zone (either calculated or measured), and one of the first set of fluid properties, the second set of fluid properties, or the first and second sets of fluid properties. The reactor model may be used to calculate an adjustment to: the intensity; the first set of fluid properties; or, any combination thereof in order to reduce the difference between the conversion calculated using the kinetic model and the target value. An adjustment to the intensity may be translated by the reactor model to an adjustment of the input power to one or more ballasts or an adjustment of the power setting of one or more ballasts. An adjustment to the first set of fluid properties may comprise an adjustment to the rate of fluid flow. When the first set of fluid properties comprises the concentration of an oxidant, an adjustment to the first set of fluid properties may further comprise an adjustment to the rate of oxidant addition to achieve a desired inlet oxidant concentration.

The reactor model may employ a fouling factor as previously described to more accurately determine the intensity within the radiation zone. The reactor model may determine the fouling factor based on an additional input signal obtained from an ultraviolet sensor. The intensity may be used to calculate a dose of ultraviolet radiation received by the fluid as it passes through the radiation zone. Ultraviolet dose is the product of the intensity (also known as the fluence rate, measured in $mW\ cm^{-2}$) and the fluid residence time (measured in seconds) and has units of $mW\ s\ cm^{-2}$ or $mJ\ cm^{-2}$. In order for the contaminant conversion to approach the target value an adjustment to the ultraviolet dose delivered to the fluid may be calculated by the reactor model, which in turn may be used to calculate an adjustment to the intensity and/or fluid flow rate. Ultraviolet dose calculation is related to fluid residence time distribution, and various models for calculating ultraviolet dose are known. A calculation of dose may be obtained from any known model, including the dosimeter model described in U.S. Pat. No. 6,564,157.

When a contaminant is treated through the addition of an oxidant, the reactor model may also relate conversion to the average oxidant concentration. The average oxidant concentration may be obtained from the first and second sets of fluid properties and may be used as an analog for the steady state hydroxyl radical (.OH) concentration within the reactor. The reactor model may then employ the steady state hydroxyl radical (.OH) concentration and the dose to determine an adjustment to the rate of oxidant addition.

The reactor model may employ an empirical model to more accurately relate system operating cost, system parameters, and conversion. A record of conversion determined by the kinetic model and adjustments to system parameters made by the reactor model may be kept in a first data set and compared with performance data collected using actual measurements of target contaminant concentration in a second data set. The comparison of the first and second data sets may be used to develop an empirical model of system performance. The empirical model may employ known techniques, such as time series analysis or neural network algorithms to more accurately predict system performance. After the initial development of the empirical model, the empirical model may be periodically updated as a fine-tuning measure using additions to the second set of data. The reactor model may incorporate the empirical model, or the reactor model may utilize information provided by the empirical model.

BRIEF DESCRIPTION OF THE DRAWINGS

Embodiments of the present invention will be described with reference to the accompanying drawings, wherein like reference numerals denote like parts, and in which.

DETAILED DESCRIPTION OF THE PREFERRED EMBODIMENTS

Figure 1:
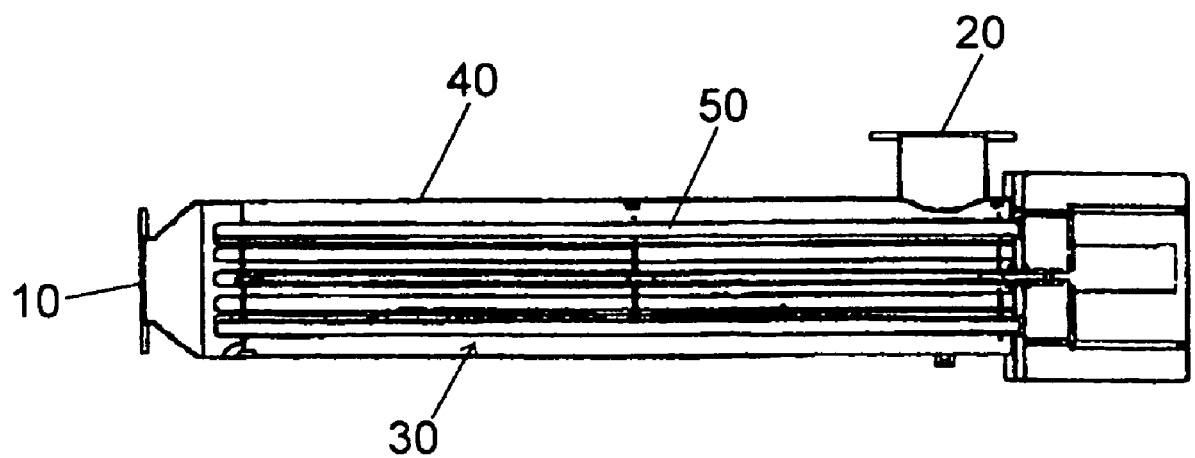
FIG. 1 is a side view of a prior art ultraviolet fluid treatment apparatus.

Referring to FIG. 1, a prior art ultraviolet fluid treatment apparatus is shown. The apparatus is used for the treatment of liquids, particularly water, and comprises a fluid inlet 10, a fluid outlet 20, and a radiation zone 30 between the fluid inlet and the fluid outlet. The radiation zone is located within an enclosed vessel 40 that may be pressurized by the fluid being treated. A plurality of ultraviolet radiation source elements 50, each comprising an ultraviolet lamp enclosed within a sleeve made from a quartz material, is located within the radiation zone 30 for providing ultraviolet radiation to the fluid.

Figure 2:
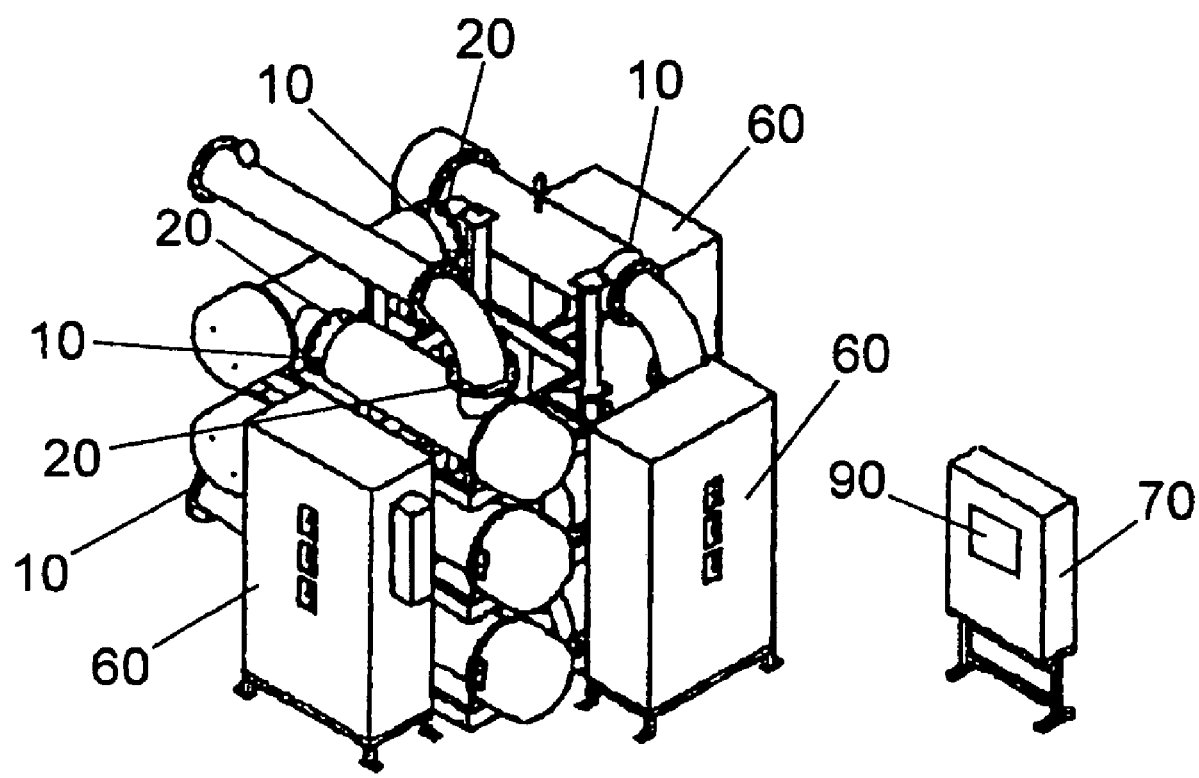
FIG. 2 is a perspective view of a plurality of the prior art fluid treatment apparatus of FIG. 1.

FIG. 2 shows a plurality of the ultraviolet fluid treatment apparatus of FIG. 1. Generally, the fluid inlets 10 and fluid outlets 20 are connected using appropriate fluid conduits to provide a serial fluid flow path through each apparatus. The ballasts (not shown), used to power the ultraviolet lamps are housed within the ballast enclosures 60. A system control center enclosure 70 is shown remote from the plurality of apparatus. The enclosure 70 houses a controller (not shown) in electronic communication with the ballasts and an operator interface 90 that displays values of the various system parameters and that may be used to manually provide adjustments of system parameters to the controller.

Figure 3:
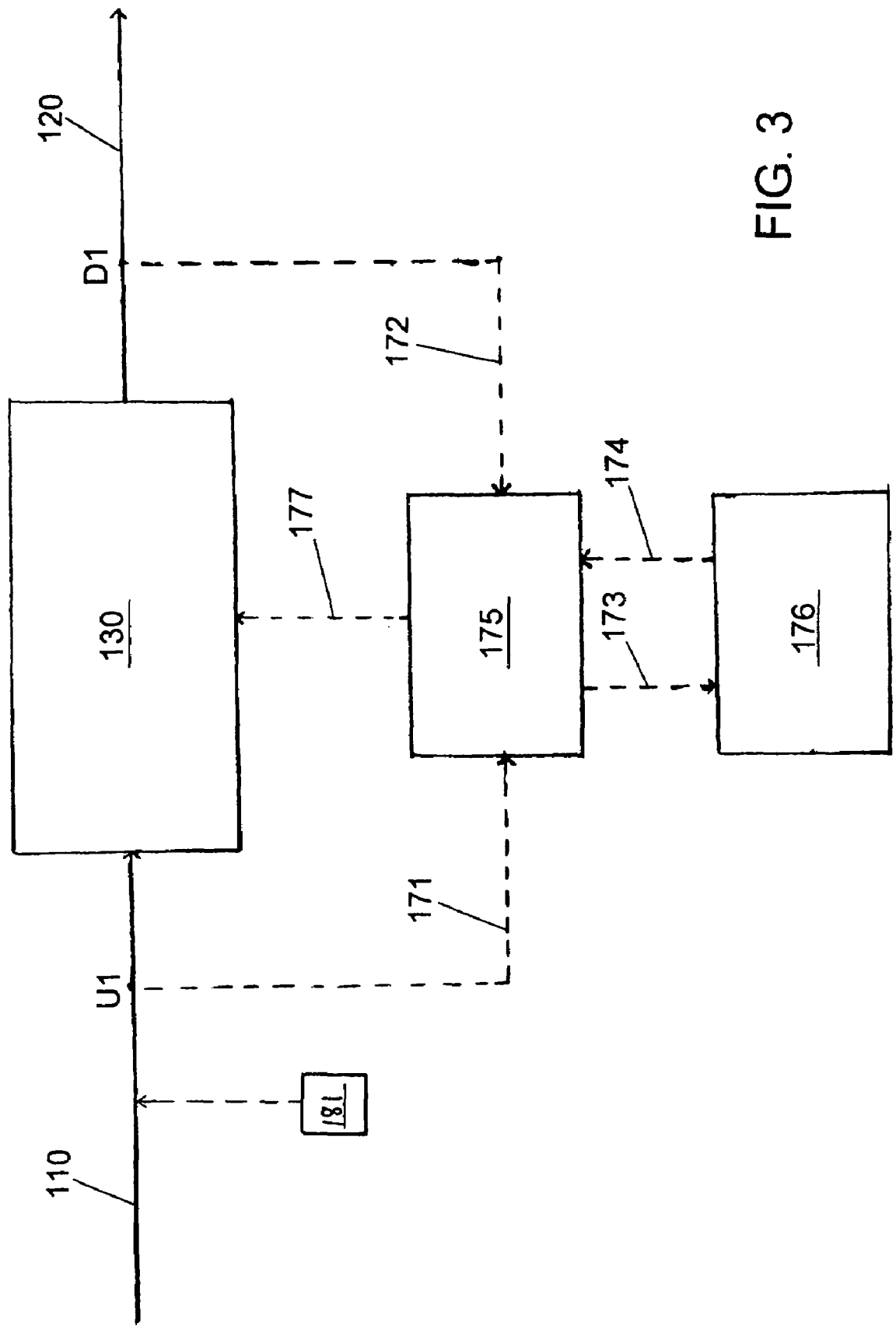
FIG. 3 is a schematic illustration of a first embodiment of a fluid treatment system according to the present invention.

A first embodiment of a fluid treatment system, shown schematically in FIG. 3, has a fluid inlet 110, a fluid outlet 120, and a radiation zone 130 between the fluid inlet and the fluid outlet. In this embodiment, the fluid is water and the fluid is treated by photolysis. Ultraviolet radiation is provided by a plurality of ultraviolet lamps (not shown), each lamp enclosed within a quartz sleeve and immersed in the fluid. A plurality of ballasts (not shown) is used to power the plurality of lamps. The lamps are low pressure or medium pressure mercury arc lamps emitting ultraviolet radiation at a wavelength of 254 nm or from about 200 nm to about 400 nm, respectively. An actinometer metering pump 181 supplies a quantity of an actinometer into the fluid. A first set of fluid properties measured upstream of the radiation zone 130, shown schematically as U1, is relayed to the control center 175 through first control center input 171. The control center 175 comprises a controller. The first set of fluid properties comprises the rate of fluid flow through the radiation zone, the transmittance of the fluid to ultraviolet light at the wavelength or wavelengths employed within the radiation zone, and a measurement of a first quantity of the actinometer. A second set of fluid properties measured downstream of the radiation zone 130, shown schematically as D1, is relayed to the control center 175 through second control center input 172. The second set of fluid properties comprises a measurement of a second quantity of the actinometer. The control center 175 relays the conversion, the target value, and the first set of fluid properties to a programmable logic device 176 through first communication line 173. The programmable logic device calculates a conversion of the contaminant using a kinetic model employing a difference between the first and second measurements of the actinometer. The programmable logic device 176 then uses a reactor model to optimize operating cost by determining an adjustment to the energy going into the fluid on a volumetric basis in order to match the conversion with the target value. An adjustment to the energy going into the fluid is translated to an adjustment to the ballast power setting. The adjustment to the ballast power setting is provided to the controller of control center 175 via second communication line 174. The controller then implements the adjustment, as shown schematically by first control center output 177.

Figure 4:
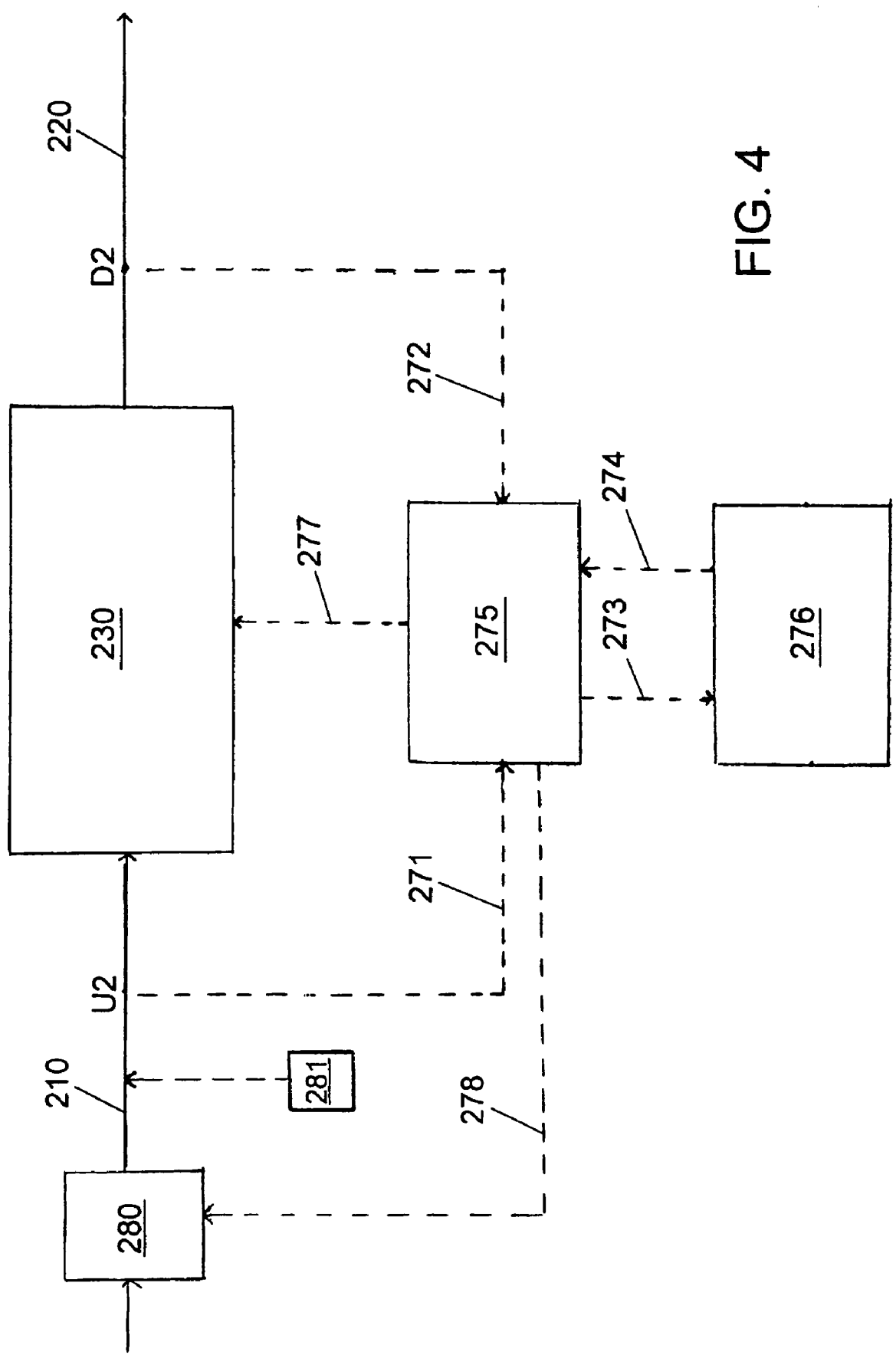
FIG. 4 is a schematic illustration of a second embodiment of a fluid treatment system according to the present invention.

A second embodiment of a fluid treatment system, shown schematically in FIG. 4, includes means to control the rate of fluid flow through the radiation zone. The second embodiment has a fluid inlet 210, a fluid outlet 220, and a radiation zone 230 between the fluid inlet and the fluid outlet. In this embodiment, the fluid is water and the fluid is treated by photolysis. Ultraviolet radiation is provided by a plurality of ultraviolet lamps (not shown), each lamp enclosed within a quartz sleeve and immersed in the fluid. A plurality of ballasts (not shown) is used to power the plurality of lamps. The lamps are low pressure or medium pressure mercury arc lamps emitting ultraviolet radiation at a wavelength of 254 nm or from about 200 nm to about 400 nm, respectively. An actinometer metering pump 281 supplies a quantity of an actinometer into the fluid. A first set of fluid properties measured upstream of the radiation zone 230, shown schematically as U2, is relayed to the control center 275 through first control center input 271. The control center 275 comprises a controller. The first set of fluid properties comprises the rate of fluid flow through the radiation zone, the transmittance of the fluid to ultraviolet light at the wavelength or wavelengths employed within the radiation zone, and a measurement of a first quantity of the actinometer. A second set of fluid properties measured downstream of the radiation zone 230, shown schematically as D2, is relayed to the control center 275 through second control center input 272. The second set of fluid properties comprises a measurement of a second quantity of the actinometer. The control center 275 relays the conversion, the target value, and the first set of fluid properties to a programmable logic device 276 through first communication line 273. The programmable logic device calculates a conversion of the contaminant using a kinetic model employing a difference between the first and second measurements of the actinometer. The programmable logic device 276 then uses a reactor model to optimize operating cost by determining an adjustment to the energy going into the fluid on a volumetric basis in order to match the conversion with the target value. The programmable logic device makes a decision whether to implement the adjustment by adjusting the ballast power setting or by adjusting the rate of fluid flow. The adjustment is provided to the controller of control center 275 via second communication line 274. The controller implements the adjustment to the ballast power setting, shown schematically by first control center output 277, or the rate of fluid flow through the radiation zone, shown schematically by second control center output 278. The rate of fluid flow is adjusted by fluid flow control element 280. The fluid flow control element 280 preferably comprises a pump having a variable speed drive that permits variation of fluid flow. Alternatively, the fluid flow control element 280 comprises a throttling or diverting valve that is used to adjust the rate of fluid flow through the radiation zone 230 of the fluid treatment system.

Figure 5:
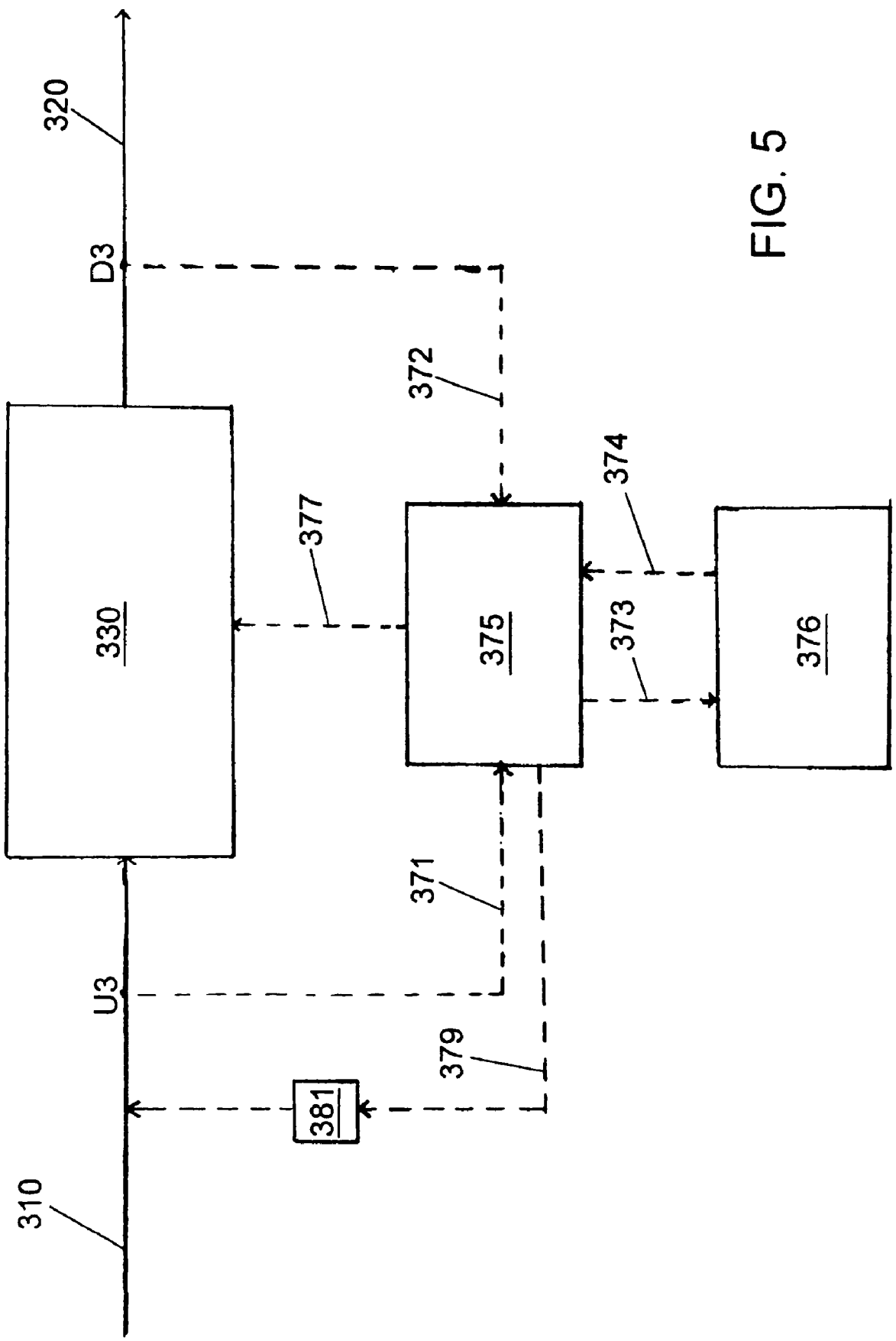
FIG. 5 is a schematic illustration of a third embodiment of a fluid treatment system according to the present invention.

A third embodiment of a fluid treatment system, shown schematically in FIG. 5, includes an oxidant injection site upstream of the radiation zone for injecting an oxidant into the fluid. In this embodiment, the fluid is water contaminated by chemical compounds and the oxidant is preferably hydrogen peroxide. The third embodiment has a fluid inlet 310, a fluid outlet 320, and a radiation zone 330 between the fluid inlet and the fluid outlet. Ultraviolet radiation is provided by a plurality of ultraviolet lamps (not shown), each lamp enclosed within a quartz sleeve and immersed in the fluid. A plurality of ballasts (not shown) is used to power the plurality of lamps. The lamps are low pressure or medium pressure mercury arc lamps emitting ultraviolet radiation at a wavelength of 254 nm or from about 200 nm to about 400 nm, respectively. A first set of fluid properties measured upstream of the radiation zone 330, shown schematically as U3, is relayed to the control center 375 through first control center input 371. The first set of fluid properties comprises the rate of fluid flow through the radiation zone, the transmittance of the fluid to ultraviolet light at the wavelength or wavelengths employed within the radiation zone, and a measurement of a first quantity of hydrogen peroxide. A second set of fluid properties measured downstream of the radiation zone 330, shown schematically as D3, is relayed to the control center 375 through second control center input 372. The second set of fluid properties comprises a measurement of a second quantity of hydrogen peroxide. The control center 375 relays the conversion, the target value, and the first set of fluid properties to a programmable logic device 376 through first communication line 373. The programmable logic device calculates a conversion of the contaminant using a kinetic model employing a difference between the first and second measurements of hydrogen peroxide. The programmable logic device 376 then uses the reactor model to optimize operating cost by determining an adjustment to the energy going into the fluid on a volumetric basis and/or the average oxidant concentration in order to match the conversion with the target value. An adjustment to the energy going into the fluid is translated to an adjustment to the ballast power setting. An adjustment to the average oxidant concentration is translated to an adjustment to the rate of oxidant addition. The adjustment or adjustments is/are provided to the controller within control center 375 via second communication line 374. The controller implements an adjustment to the ballast power setting, shown schematically by first control center output 377, and/or the rate of oxidant addition, shown schematically by second control center output 379. The second control center output 379 is connected to an oxidant dosing device 381, which is preferably a peroxide metering pump, that permits variation of the rate of oxidant addition.

A fourth embodiment of a fluid treatment system (not shown), includes an oxidant injection site upstream of the radiation zone for injecting an oxidant into the fluid as shown in FIG. 5 and a fluid flow control element as shown in FIG. 4. In this embodiment, the programmable logic device makes a decision whether to implement an adjustment to the energy going into the fluid on a volumetric basis by adjusting the ballast power setting or by making an adjustment to the rate of fluid flow, as described above with reference to the second embodiment.

Figure 6:
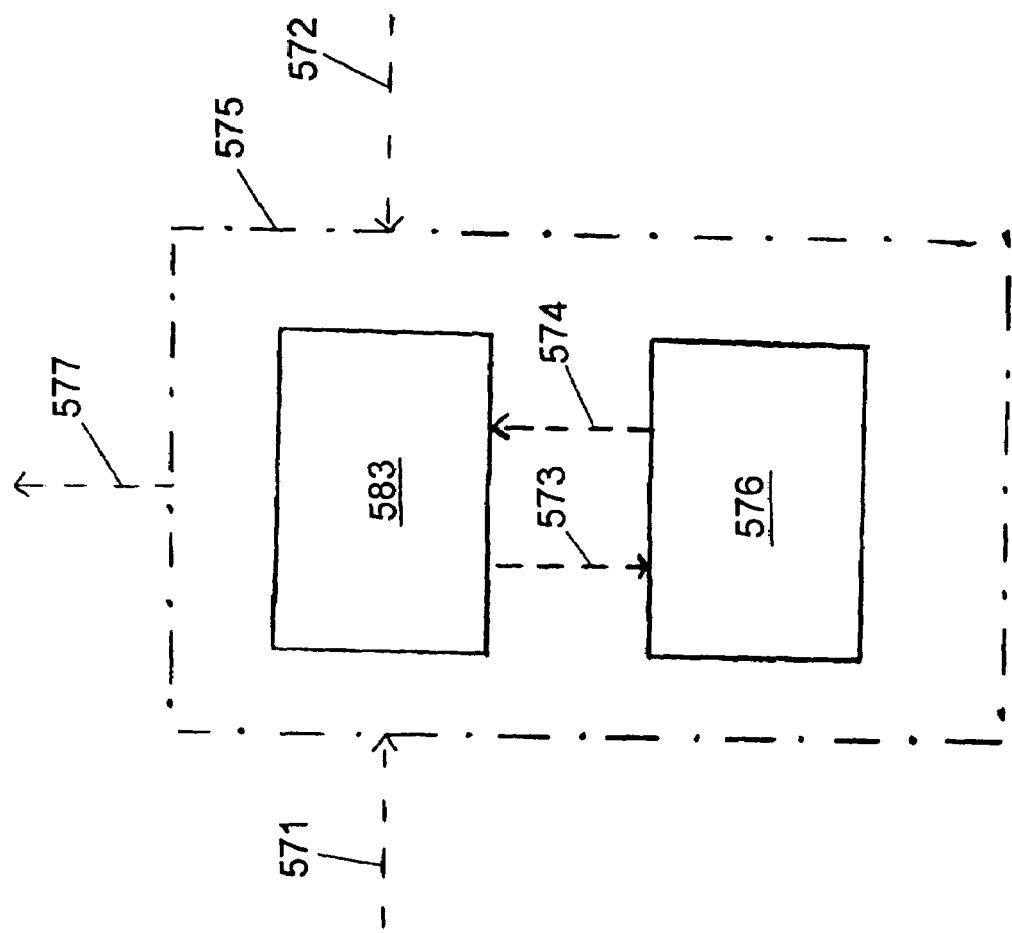
FIG. 6 is a schematic illustration of a control center according to the present invention.

Referring to FIG. 6, a control center 575 comprises a controller 583 and a programmable logic device 576. The controller 583 and the programmable logic device 576 are in bi-directional communication with one another through first communication line 573 and second communication line 574. Preferably, the control center 575 includes an enclosure and the controller 583 and programmable logic device 576 are located within the enclosure. More preferably, the controller 583 and the programmable logic device 576 are co-located within the enclosure. The control center 575 receives inputs from first control center input 571 and second control center input 572. The control center outputs a signal to adjust one or more system parameters through first control center output 577 and other control center outputs as needed.

Figure 7:
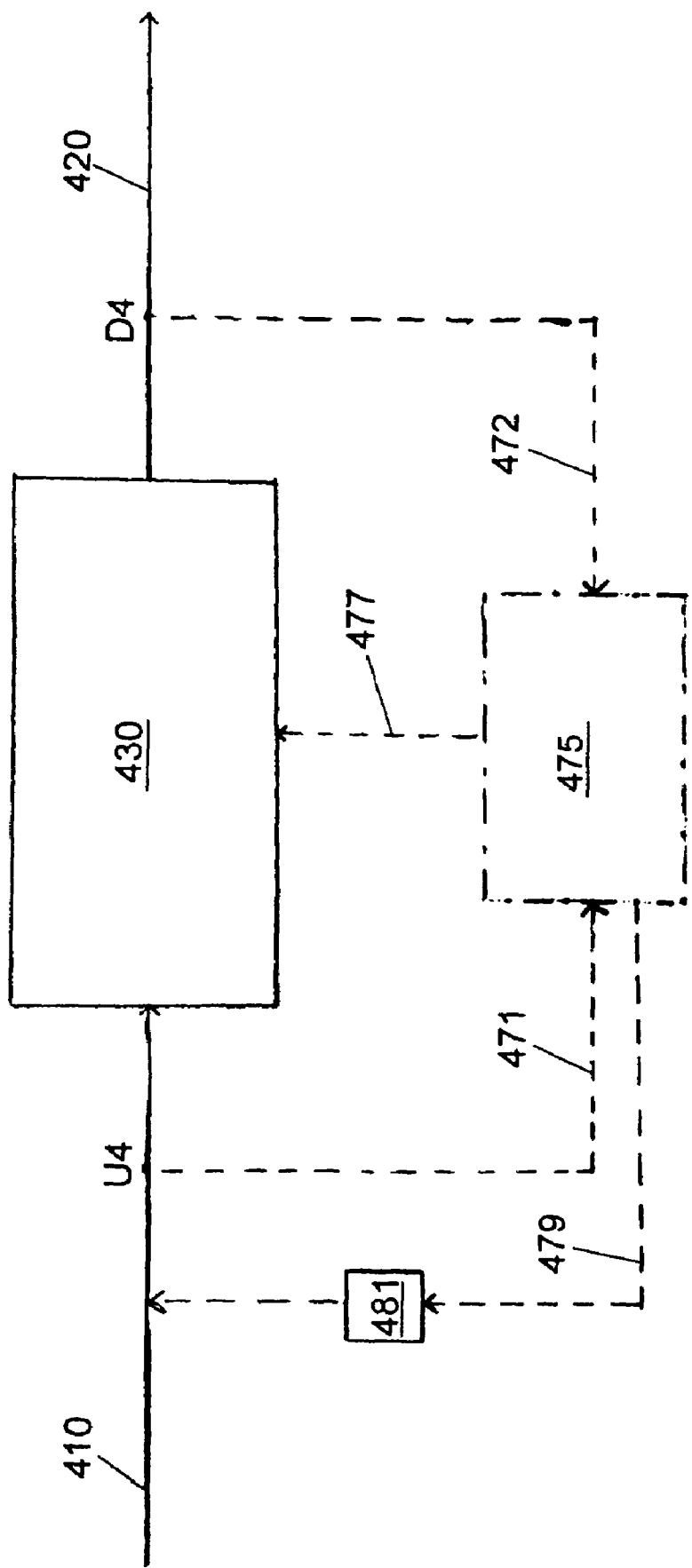
FIG. 7 is a schematic illustration of a fourth embodiment of a fluid treatment system according to the present invention incorporating the control center of FIG. 6.

A fifth embodiment of a fluid treatment system, shown schematically in FIG. 7, includes an oxidant injection site upstream of the radiation zone as provided in the third and fourth embodiments and a control center according to FIG. 6. In this embodiment, the fluid is water contaminated by chemical compounds and the oxidant is preferably hydrogen peroxide. The fifth embodiment has a fluid inlet 410, a fluid outlet 420, and a radiation zone 430 between the fluid inlet and the fluid outlet. Ultraviolet radiation is provided by a plurality of ultraviolet lamps (not shown), each lamp enclosed within a quartz sleeve and immersed in the fluid. A plurality of ballasts (not shown) is used to power the plurality of lamps. The lamps are low pressure or medium pressure mercury arc lamps emitting ultraviolet radiation at a wavelength of 254 nm or from about 200 nm to about 400 nm, respectively. It is also possible to use other UV emitting sources, such as dielectric barrier discharge (DBD) lamps, xenon lamps, eximer lamps, and the like. A first set of fluid properties measured upstream of the radiation zone 430, shown schematically as U4, is relayed to the control center 475 through first control center input 471. The first set of fluid properties comprises the rate of fluid flow through the radiation zone, the transmittance of the fluid to ultraviolet light at the wavelength or wavelengths employed within the radiation zone, and a measurement of a first quantity of hydrogen peroxide. A second set of fluid properties measured downstream of the radiation zone 430, shown schematically as D4, is relayed to the control center 475 through second control center input 472. The second set of fluid properties comprises a measurement of a second quantity of hydrogen peroxide. The control center 475 includes a programmable logic device that calculates a conversion of the contaminant using a kinetic model employing a difference between the first and second measurements of hydrogen peroxide concentration. The programmable logic device then uses the reactor model to optimize operating cost by determining an adjustment to the energy going into the fluid on a volumetric basis and/or the average oxidant concentration in order to match the conversion with the target value. An adjustment to the energy going into the fluid is translated to an adjustment to the ballast power setting. An adjustment to the average oxidant concentration is translated to an adjustment to the rate of oxidant addition. The control center 475 includes a controller that implements an adjustment to the ballast power setting, shown schematically by first control center output 477, and/or the rate of oxidant addition, shown schematically by second control center output 479. The second control center output 479 is connected to an oxidant dosing device 481, which is preferably a peroxide metering pump, that permits variation of the rate of oxidant addition. The control center 475 preferably comprises a controller and a programmable logic device that are co-located.

Kinetic Model

The kinetic model used in the treatment of a chemical contaminant C in aqueous solution by photo-oxidation using hydrogen peroxide ($H_2O_2$) will be described herein by way of example. The kinetic model can be approximated in terms of the following simple reaction scheme, making reference to the following sources:

1. Stefan, M. I.; Hoy, A. R., and Bolton, J. R. 1996. Kinetics and mechanism of the degradation and mineralization of acetone in dilute aqueous solution sensitized by the UV photolysis of hydrogen peroxide. *Environ. Sci. Technol.* 30 (7), 2382-2390.
2. De Laat, J.; Berger, P.; Poinot, T.; Karpel Vel Leitner, N., and Doré, M. 1997. Modeling the oxidation of atrazine by $H_2O_2$/UV. Estimation of kinetic parameters. *Ozone Sci. Engng.* 19, 395-408.
3. Onstein, P.; Stefan, M. I., and Bolton, J. R. 1999. Competition kinetics method for the determination of rate constants for the reaction of hydroxyl radicals with organic pollutants using the UV/H2O2 advanced oxidation technology. The rate constants for tert-butylformate ester and 2,4-dinitrophenol. *J. Adv. Oxid. Technol.* 4 (2), 231-236.

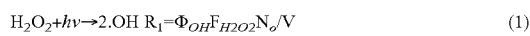

$$H_2O_2 + h\nu \rightarrow 2 \cdot OH \quad R_1 = \Phi_{OH} F_{H2O2} N_o / V \quad (1)$$

$$\cdot OH + C \rightarrow products \quad R_2 = k_{C,OH}[C][\cdot OH] \quad (2)$$

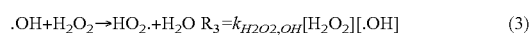

$$\cdot OH + H_2O_2 \rightarrow HO_2 \cdot + H_2O \quad R_3 = k_{H2O2,OH}[H_2O_2][\cdot OH] \quad (3)$$

$$\cdot OH + S \rightarrow products \quad R_4 = k_{S,OH}[S][\cdot OH] \quad (4)$$

where $R_{1-4}$ are the rates for reactions 1-4, $k_{X,OH}$ are the rate constants for the reactions of those specific compounds with the .OH radical ($M^{-1}s^{-1}$), $\Phi_{OH}=1.0$, is the quantum yield of the .OH radical generation during the photolysis of $H_2O_2$, $F_{H2O2}$ is the fraction of light absorbed by $H_2O_2$ over the irradiation wavelength range, $N_o$ is the incident photon flow (Ein $s^{-1}$), V is the irradiated volume (L), and [C] and [S] are the molar concentrations of the contaminant and any potential .OH radical scavenger in the water other than C and $H_2O_2$, respectively. The contaminant is assumed to decay only through the .OH radical oxidation processes. At very short irradiation times, the following assumptions hold:

a) The change in the concentration of $H_2O_2$ is small to minimal, therefore $F_{H2O2}\sim$constant;
b) The water absorption spectrum does not change significantly, therefore $F_{H2O2}\sim$constant;
c) No significant levels of reaction intermediates are generated from either the original contaminant or the water constituents that are not accounted for as .OH radical scavengers in the above reaction scheme, therefore $$\sum_i k_{Si,OH}[S_i]_o$$

in equation 5 is approximately constant, and is herein referred to as the fluid background term.

From the steady-state approximation, d [.OH]/d t=0, applied to the above reaction scheme, one can express the initial rate of contaminant decay as [refs 1,3]:

$$-\frac{d[C]}{dt}\bigg|_{t=0} = \frac{k_{C,OH}[C] \times \phi_{OH} F_{H_2O_2} N_o / V}{k_{C,OH}[C]_o + k_{H_2O_2,OH}[H_2O_2]_o + \sum_i k_{si,OH}[S_i]_o} \quad (5)$$

Often, the contaminant is light sensitive and undergoes direct UV photolysis, along with the OH radical-induced oxidation. In such cases, the general expression of the contaminant decay comprises both the UV photolysis and the UV oxidation term as shown in equation 6:

$$-\frac{d[C]}{dt}\bigg|_{t=0} = \frac{1}{V}\left[\begin{array}{l}\sum_\lambda \frac{N_{o,\lambda}\Phi_\lambda^C \varepsilon_\lambda^C}{a_\lambda}(1-10^{-a_\lambda l}) + \\ \frac{k_{C,OH} \times \phi_{OH} F_{H2O2} N_o}{k_{C,OH}[C]_o + k_{H_2O_2,OH}[H_2O_2]_o + \sum_i k_{Si,OH}[S_i]_o}\end{array}\right][C] \quad (6)$$

where $\Phi^C_\lambda$ and $\varepsilon^C_\lambda$ are the quantum yield for the UV photolysis of contaminant C and its molar absorption coefficient at wavelength $\lambda$, respectively, and $N_{o,\lambda}$ and $\alpha_\lambda$ are the incident photon flow and fluid absorption coefficient ($cm^{-1}$), which contains the contaminant C, at wavelength $\lambda$, respectively.

Therefore, when the UV photolysis of contaminant C occurs concomitantly with the OH radical-based oxidation, the kinetic model is based on equation 6.

The pseudo-first order rate constant ($k_1$, $s^{-1}$) for the contaminant decay through the .OH radical oxidation can be approximated by equation 7:

$$k_1 = \frac{k_{C,OH}\phi_{OH} F_{H_2O_2} N_o / V}{k_{C,OH}[C]_o + k_{H_2O_2,OH}[H_2O_2]_o + \sum_i k_{si,OH}[S_i]_o} \quad (7)$$

A similar expression is derived for the rate constant of the contaminant decay through the combined processes, which includes the photochemical parameters of contaminant C mentioned above.

If the fluid properties (for example: ultraviolet light absorbance spectrum; pH; alkalinity; dissolved natural organic matter as TOC, or any potential .OH radical scavengers) and the rate constants for the reactions with the .OH radical $k_{X,OH}$ are known (as well as $\Phi^C_\lambda$ and $\varepsilon^C_\lambda$ if the UV photolysis occurs), the rate constant $k_1$ can be calculated for a given concentration of $H_2O_2$. The calculation of the fraction of light absorbed by hydrogen peroxide depends on the spectral distribution of the lamp, ultraviolet absorption spectrum of the fluid, and molar absorption coefficients of $H_2O_2$ ($\varepsilon_\lambda$, $M^{-1}cm^{-1}$):

$$F_{H_2O_2} = \sum_\lambda N_{i,\lambda} \frac{\varepsilon^\lambda_{H_2O_2}[H_2O_2](1-10^{-a\lambda l})}{a_\lambda} \quad (8)$$

where $a_\lambda = \varepsilon_{\lambda,H2O2}[H_2O_2]+\alpha_\lambda$ is the solution absorbance ($cm^{-1}$) at $\lambda$, and $\alpha_\lambda$ is the absorption coefficient ($cm^{-1}$) of the fluid which contains the contaminant C, $\varepsilon_{\lambda,H2O2}$ is the molar absorption coefficient of hydrogen peroxide at $\lambda$, and l is the pathlength traversed by the light.

The rate constants $k_{X,OH}$ may be determined using constants known in the art. Alternatively, rate constants $k_{X,OH}$ may be determined in the laboratory. Some published kinetic rate constants for reaction of chemical contaminant C in aqueous solution with hydroxyl radicals (.OH) are provided in Table 1 below, taken from the following source:

Buxton, G. V.; Greenstock, C. L.; Helman, W. P., and Ross, A. B. 1988. Critical Review of Rate Constants for Reactions of Hydrated Electrons, Hydrogen Atoms and Hydroxyl Radicals (.OH/.O$^-$) in Aqueous Solution. *J. Phys. Chem. Ref. Data* 17 (2), 513-886.

TABLE 1

Published kinetic rate constants for reaction of chemical contaminant C in aqueous solution with hydroxyl radicals (•OH).

| Chemical contaminant | Rate constant $k_{X,OH}$, M$^{-1}$ s$^{-1}$ |
|---|---|
| 1,4-Dioxane | $2.8 \times 10^9$ |
| Trichloroethylene (TCE) | $4.2 \times 10^9$ |
| Methyl tert-butyl ether (MTBE) | $1.6 \times 10^9$ |
| Pentachlorobenzene (PCB) | $4 \times 10^9$ |

The fluid background term $$\sum_i k_{Si,OH}[S_i]_o$$

and/or background kinetic rate constants, $k_{Si,OH}$ are generally not easily obtained from published sources due to variable background water quality. Preferably, the fluid background term is determined experimentally in a laboratory using a sample of the fluid being treated. By way of example, the determination of the fluid background term is described below for the scavenging of hydroxyl radicals by background species such as organic and inorganic species reactive toward OH radicals.

The fluid background term, or .OH radical demand of the water background $$\left(\sum_i k_{s_i,OH}[S_i]_o\right)$$

in the kinetic equations 5-7 described above, may be determined experimentally by a competition kinetics method using a reference compound R with a known rate constant for reaction with the .OH radical. While, the reference compound R may be selected from Table 1, those of skill in the art will appreciate that it is possible to utilize other reference compounds not specifically mention in Table 1. Preferably, and for purposes of this example, the reference compound R is 1,4-dioxane. The rate constants for the photo-induced degradation of reference compound R are determined experimentally in an actual sample of the fluid being treated and in a prescribed fluid, for example ultrapure water (for example, milliQ™ water known for use in laboratories) in the presence of a known $H_2O_2$ concentration. The experiments can be performed with either monochromatic or polychromatic light using a collimated beam apparatus, as is known to persons skilled in the art, under controlled incident irradiance and using similar irradiation geometries. For example, the experiments may be conducted in a stirred dish, and the irradiation geometry may comprise the irradiated volume, depth of fluid in the dish, and distance of the surface of the fluid from the ultraviolet lamp in the collimated beam apparatus. Based on the experimental rate constants, and equation 7, where the contaminant C is replaced by the reference compound R, the following expression can be derived:

$$\frac{k_1^{milliQ}}{k_1^{water}} = \qquad (9)$$

-continued
$$\frac{F_{H_2O_2}^{milliQ}}{F_{H_2O_2}^{water}} \times \frac{k_{R,OH}[R]_o^{water} + k_{H_2O_2,OH}[H_2O_2]_o^{water} + \sum_i k_{s_i,OH}[S_i]_o}{k_{R,OH}[R]_o^{milliQ} + k_{H_2O_2,OH}[H_2O_2]_o^{milliQ}}$$

If the incident irradiances E (which are proportional to $N_o$) are distributed differently across the dish in the two experiments, the term on the right side of equation 9 should be multiplied by the ratio $E^{milliQ}/E^{water}$. In the prescribed fluid the reference compound R and $H_2O_2$ are the only compounds reacting with the .OH radicals. It is appreciated that the prescribed fluid may contain dissolved carbon dioxide ($CO_2$) that reacts with .OH radicals. In this case, a term may be added to the denominator on the right side of equation 9 to refine the equation. However, for ultrapure water its contribution is negligible, given both the low concentration of dissolved carbon dioxide and the small rate constant for the reaction of carbon dioxide with the .OH radical ($<1 \times 10^6$ M$^{-1}$s$^{-1}$ [ref 4]).

Then, the .OH radical demand (units s$^{-1}$) of the fluid sample is calculated as:

$$\sum_i k_{s_i,OH}[S_i]_o = \qquad (10)$$
$$\frac{k_1^{milliQ}}{k_1^{water}} \times \frac{F_{H_2O_2}^{water}}{F_{H_2O_2}^{milliQ}} \times \left(k_{R,OH}[R]_o^{milliQ} + k_{H_2O_2,OH}[H_2O_2]_o^{milliQ}\right) -$$
$$\left(k_{R,OH}[R]_o^{water} + k_{H_2O_2,OH}[H_2O_2]_o^{water}\right)$$

All parameters in equation 10 are either known from the literature or are based on the experimental measurements. For example, when R is 1,4-dioxane, $k_{diox,OH}=2.8 \times 10^9$ M$^{-1}$ s$^{-1}$, $k_{H2O2,OH}=2.7 \times 10^7$ M$^{-1}$ s$^{-1}$, and the water absorption spectrum and the molar absorption coefficients of $H_2O_2$ are determined experimentally. Alternatively, the OH radical demand (units s$^{-1}$) of the actual sample of the fluid being treated can be calculated from equation 7 using the rate constant for the photo-induced degradation of reference compound R $k_1$ determined in the actual sample of fluid being treated, where the time-dependent entities in equation 7, such as $F_{H2O2}$, $k_{C,OH}[C]$ (where C is the reference compound C) and $k_{H2O2,OH}[H_2O_2]$ are determined and calculated at each experimental irradiation time of the actual sample of the fluid being treated. Thus, the OH radical demand of the fluid being treated is the average of all its values calculated at each irradiation time.

If the fluid contains the contaminant C, the background term $\Sigma k_{Si,OH}[Si]_o$ comprises the contribution of the contaminant C. In practice, given the very low levels of contaminant C in the fluid as compared to the other fluid constituents, such as dissolved organic matter, and inorganic species, the contribution of contaminant C to the background term is negligible.

Such an analysis is valid only for short irradiation times, where the assumptions outlined above for the theoretical expression of a rate constant (equation 7) hold. The background term calculated above may be influenced by the presence of contaminant C; however, in practice, the impact on the background term is usually negligible.

A potential source of error in the experiments is the measurement of ultraviolet light absorbance, especially when the absorbance is low, since the values are difficult to measure accurately. Preferably, long pathlength quartz cells are used, and several readings are taken to minimize the likelihood of errors.

The value of the fluid background term calculated using the above method for several samples of actual fluid is provided in Table 2 below:

TABLE 2 value of the fluid background term calculated for several samples of actual fluid

| Fluid Sample ID | Fluid background term ($s^{-1}$) |
| --- | --- |
| A | $3.34 \times 10^4$ |
| B | $9.20 \times 10^4$ |
| C | $5.80 \times 10^4$ |

Reactor Model

The reactor model used for optimization of system parameters in the treatment of a chemical contaminant C in aqueous solution by photo-oxidation using hydrogen peroxide ($H_2O_2$) will be described herein by way of example. The reactor model utilizes the electrical energy per order (EE/O) parameter. This approach comprises the following steps:

1. Measure $\Delta[H_2O_2]$.
2. Calculate Log ($C_0/C$).
3. Calculate EE/O of contaminant at $[H_2O_2]_{avg}$.
4. Update EE/O vs. $[H_2O_2]$ correlation.
5. Update operating cost vs. EE/O and $[H_2O_2]$ correlation.
6. Calculate optimum $[H_2O_2]$ that results in minimum operating cost for a given treatment level.

If the fluid background term for the water (i.e., $\Sigma k_s[S]$) is known and assumed not to change significantly (i.e., is constant) and it comprises the contribution of the contaminant C, as discussed above, and the other kinetic constants are known, then the appropriate kinetic model based on equation 5 can be utilized to predict the reduction of the contaminant based on the measured reduction of peroxide. The basics of the kinetic model are comprised in the general equation 6, which applies to a contaminant that undergoes both direct UV photolysis and OH radical-induced oxidation. If the contaminant C decays through the OH radical-induced oxidation, the integrated form of the rate equation is given by:

$$\log \frac{C_0}{C_t} = \frac{k_{C,OH} \phi_{OH} F_{H2O2} N_0 t}{\ln 10 \, V \left( k_{H_2O_2}[H_2O_2]_{avg} + \sum_i k_{Si,OH}[S_i] \right)} \quad (11)$$

The background term includes the contribution of the contaminant C, since the fluid sample tested to determine the OH radical background demand usually originates from the fluid that needs to be treated for contaminant removal. The model uses the average of the $H_2O_2$ concentrations at treatment times 0 and t. It should be noted that the term $k_{H2O2,OH}[H_2O_2]_{avg}$ could be one or more orders of magnitude smaller than $\Sigma k_{Si,OH}[Si]$ due to the following factors:

a. High OH radical demand of the fluid background
b. Low concentrations of $H_2O_2$ generally used.
c. Small value of $k_{H2O2,OH}$ as compared to most of the $k_{Si,OH}$ values.

Therefore, it is conceivable to assume that $H_2O_2$ decays primarily through reaction (1). The rate of hydrogen peroxide decay through the UV photolysis (reaction 1) is:

$$-\frac{d[H_2O_2]}{dt} = \frac{\phi_{H2O2} F_{H2O2} N_0}{V} \quad (12)$$

Given that the quantum yield for the decay of $H_2O_2$ through the photochemical step is $\phi_{H2O2}=0.5$, and the decay follows zero-order kinetics, equation 11 can be rearranged as:

$$\log \frac{C_0}{C_t} = \frac{2\Delta[H_2O_2] \times k_{C,OH}}{\ln 10 \left( k_{H2O2,OH}[H_2O_2]_{avg} + \sum_i k_{Si,OH}[S_i] \right)} \quad (13)$$

Equation 13 is the basis of the algorithm that allows the calculation of the order of magnitude of contaminant removal through the OH radical-induced processes, from the change in the concentration of hydrogen peroxide. The equation can be generalized for the decay of the contaminant C through both direct UV photolysis and OH radical-induced processes, and is valid for both monochromatic and polychromatic light sources.

The log reduction can therefore be predicted and compared with the set-point level. The log reduction will be a function of the change in peroxide concentration as well as some known kinetic constants.

For a given system (i.e., given fluid background term and other kinetic parameters) the log reduction is also a function of the water ultraviolet transmittance (UVT), system power, peroxide concentration, lamp hours, water temperature, and ballast power level. All these parameters, except for the water temperature are accounted for in equations 6 and 8. In a more general way, that is expressed as:

$$\text{Log}(C_0/C) = f(UVT, P(kW), [H_2O_2], HRS, \text{Temp.}, P(\%)) \quad (14)$$

The electrical efficiency of a UV treatment system (i.e., UV reactor, lamp, water quality, and chemical contaminant) in the removal of contaminant C through a first order kinetics law is best described by the Electrical Energy per Order ($E_{EO}$) parameter [Bolton, J. R., Bircher, K. G., Tumas, W., and Tolman, C. A. 2001. "Figures-of-merit for the technical development and application of advanced oxidation technologies for both electric- and solar-driven systems". *Pure Appl. Chem.* 73 (4), 627-637]. This term describes the electrical energy (kWh) required to treat a volume of water (1000 gallons or 1 m³) to a specified treatment level (one order of magnitude reduction of target contaminant). The typical units of $E_{EO}$ are kWh/1000 gallons/order or kWh/m³/order. The formula for calculating this parameter is:

$$E_{EO} = \frac{P \times 1000}{Q \times 60 \times \log \frac{C_0}{C_t}} \quad (15)$$

where P (kW) and Q (gpm) are the system power and flow rate, respectively, and 1000 and 60 are conversion factors to kgal and hr, respectively. Therefore, the $E_{EO}$ can be linked directly to the change in the concentration of hydrogen peroxide, as shown in equation 16:

$$E_{EO} = \frac{19.19P \times \left(k_{H2O2,OH}[H_2O_2]_{avg} + \sum k_{Si,OH}[S_i]\right)}{\Delta[H_2O_2] \times k_{C,OH} \times Q} \quad (16)$$

The $E_{EO}$ term is a comprehensive measure of reactor electrical efficiency. The $E_{EO}$ value for a photoreactor is a function of the efficiency of photon generation (i.e., lamp electrical efficiency), the efficiency of photon delivery to the target species (for example: in photolysis, the target contaminant; and, in photo-oxidation, the oxidant) and the fundamental kinetic parameters of the process.

Using the predicted log reduction of the contaminant C, the $E_{EO}$ for the contaminant can be calculated. Therefore, either the log of contaminant removal or the $E_{EO}$ can be used as a set point for the treatment process, which can be compared with the actual value through the change in the $H_2O_2$ concentration, $\Delta[H_2O_2]$, which is measured on-line.

The $E_{EO}$ parameter has been related to the fundamental kinetic parameters and is thus shown to be a function of hydrogen peroxide concentration [Bolton, J. R., Bircher, K. G., Tumas, W., and Tolman, C. A. 2001. "Figures-of-merit for the technical development and application of advanced oxidation technologies for both electric- and solar-driven systems". *Pure Appl. Chem.* 73 (4), 627-637]. This relationship is described as:

$$E_{EO} = \frac{19.19P \times \left(k_{H2O2,OH}[H_2O_2]_{avg} + \sum k_{Si,OH}[S_i]\right)}{\phi_{H_2O_2} F_{H_2O_2} N_0 k_{C,OH}} \quad (17)$$

Optimal adjustment of the UV treatment system parameters relies on the correlation of $E_{EO}$ with the hydrogen peroxide concentration. Manipulation of equations 8 and 12 provides the correlation between the change in hydrogen peroxide concentration (i.e., $\Delta[H_2O_2]$) and the initial or upstream hydrogen peroxide concentration. This correlation is given as:

$$\Delta[H_2O_2] = \left(\frac{\phi_{H_2O_2} \varepsilon_{H_2O_2}(1 - 10^{-al})N_0 t}{aV}\right)[H_2O_2]_0 = B[H_2O_2]_0 \quad (18)$$

where B is taken to be relatively constant and represents the bracketed term in the middle of equation 18. It is seen that the change in hydrogen peroxide concentration is a function of the kinetic constants, quantum yield and molar absorption coefficient, the reactor constant, optical pathlength, as well as the applied photon flux, water absorbance, flow rate (Q=V/t) and hydrogen peroxide concentration. Since $\Delta[H_2O_2]$ and $[H_2O_2]_0$ are measurable quantities, the ratio of $\Delta[H_2O_2]$ to $[H_2O_2]_0$ can be utilized as a constant and is descriptive of the reactor performance at the time of the measurements. That is:

$$\frac{\Delta[H_2O_2]}{[H_2O_2]_0} = \left(\frac{\phi_{H_2O_2} \varepsilon_{H_2O_2}(1 - 10^{-al})N_0 t}{aV}\right) = B \quad (19)$$

This assumption is valid for small changes in hydrogen peroxide concentration that do not significantly change the water UV absorbance. Substituting B into equation 17 provides the correlation between $E_{EO}$ and hydrogen peroxide concentration.

$$E_{EO} = \frac{19.19P \times \left(k_{H2O2,OH}[H_2O_2]_0 + \sum_i k_{Si,OH}[S_i]\right)}{B[H_2O_2]_0 \times k_{C,OH} \times Q} \quad (20)$$

Ongoing operation and maintenance (O&M) costs comprise electricity cost, lamp replacement cost, and, in cases where hydrogen peroxide is used as an oxidant, hydrogen peroxide cost and quenching agent (e.g., sodium hypochlorite) cost for the removal of the excess hydrogen peroxide exiting the radiation zone. While it will be understood that there are numerous methods available to remove the residual hydrogen peroxide, the following example of adding sufficient sodium hypochlorite to quench the hydrogen peroxide is the preferred method.

The daily O&M costs are calculated as the sum of the cost components using the following equations:

$$ElectricalCost\left(\frac{\$}{hr}\right) = P(kW) \div EnergyCost\left(\frac{\$}{kWh}\right) \quad (21)$$

$$CostofHydrogenPeroxide\left(\frac{\$}{hr}\right) = \frac{[H_2O_2]\left(\frac{mg}{L}\right) \times Q\left(\frac{L}{hr}\right) \times 4.5\left(\frac{\$}{gal}\right)}{600\left(\frac{mg}{mL}\right) \times 3785\left(\frac{mL}{gal}\right)} \quad (22)$$

$$CostofChlorine\left(\frac{\$}{hr}\right) = \frac{[H_2O_2]\left(\frac{mg}{L}\right) \times 2.1\left(\frac{mg\ Cl_2}{mg\ H_2O_2}\right) \times Q\left(\frac{L}{hr}\right) \times 150\left(\frac{\$}{ton}\right)}{454,000\left(\frac{mg}{lb}\right) \times 2000\left(\frac{lb}{ton}\right)} \quad (23)$$

$$CostofLampReplacement\left(\frac{\$}{hr}\right) = \frac{No.\ OperatingLamps \times Cost\left(\frac{\$}{Lamp}\right)}{LampLife(hr)} \quad (24)$$

Figure 8:
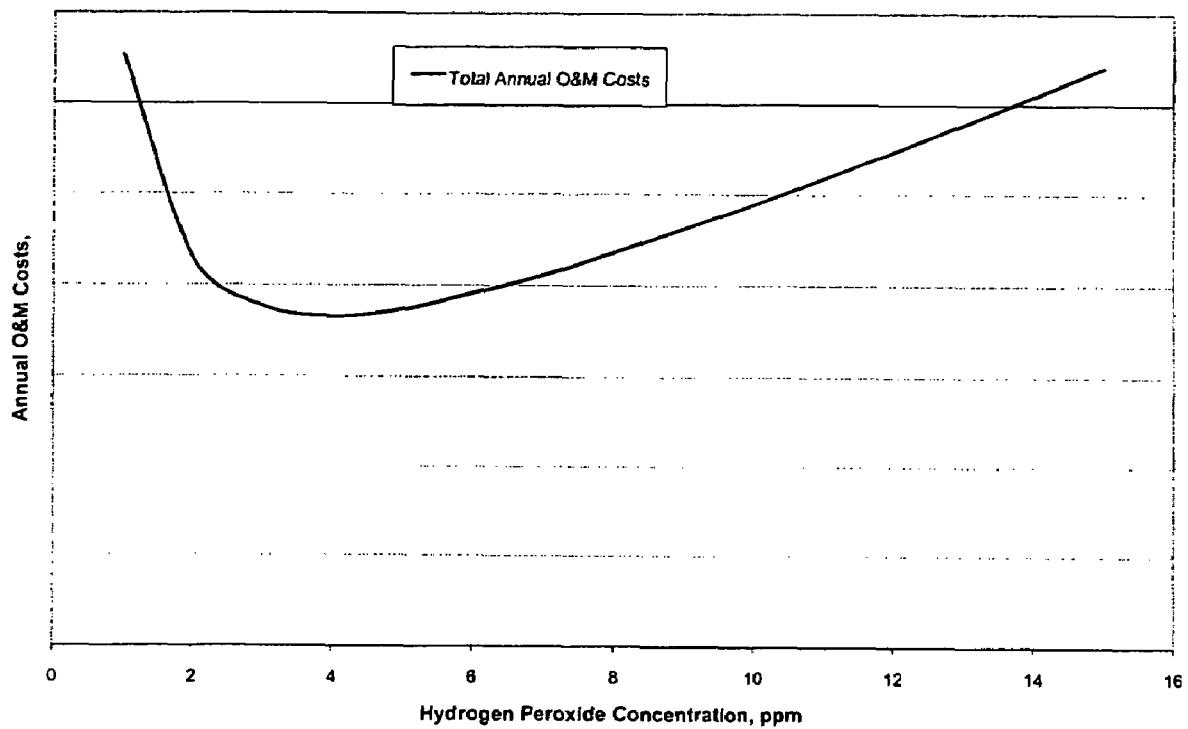
FIG. 8 illustrates a typical variation of O&M costs with hydrogen peroxide concentration and indicates that the operating cost can be minimized by operating with about 4 ppm hydrogen peroxide.

The UV system power (P) is determined from the selected $E_{EO}$ value together with the flow rate and required log reduction. All other terms in the cost equations are either known or can be determined. Therefore, the total daily O&M cost can be expressed as a function of the concentration of hydrogen peroxide. Utilizing this correlation with the appropriate constraints on power levels, flow rates, peroxide concentration, contaminant destruction, etc., the daily O&M cost can be minimized. The peroxide concentration for which these costs are a minimum is then used to determine the required system power and these parameters can then be communicated to the controller which implements the adjustments to the system parameters (i.e., ballast power settings and rate of oxidant addition). FIG. 8 illustrates a typical variation of O&M costs with hydrogen peroxide concentration and indicates that the operating cost can be minimized by operating with about 4 ppm hydrogen peroxide. This result is, of course, dependent on all the kinetic, water quality, reactor and cost factors described in the preceding analysis. Whereas this model description has been illustrated for a monochromatic system operating via the OH radical-induced process the equations can be generalized for the decay of the contaminant C through both direct UV photolysis and OH radical-induced processes, and are valid for both monochromatic and polychromatic light sources.

It can be seen that precise knowledge of the contaminant concentration is not required. The only equation requiring the contaminant concentration is that which calculates the total demand for hydroxyl radicals. The contribution to this demand from the contaminant is usually insignificant. It is expected that the order of magnitude of the contaminant concentration will be known and this is all that is required to predict the performance of the system.

This model development has assumed that the quartz sleeves are not fouled. By comparing an intensity measurement obtained from an ultraviolet sensor with a calculated intensity value, a sleeve fouling factor can be determined. The calculated intensity for a given reactor design (geometry of the radiation zone) is a function of the ultraviolet transmittance of the fluid, lamp power (i.e., ballast power setting), lamp age and fluid temperature. If the measured intensity is less than the calculated intensity, the discrepancy is due to fouled sleeves. The fouling factor would be accounted for in the overall reactor efficiency parameter that would ultimately affect the EE/O: [$H_2O_2$] correlation and the minimum operating cost. A comparison of this minimum operating cost can be made with that for which the fouling factor is increased to 1.0 (or other specified set-point). This comparison in operating cost quantifies the on-going cost associated with not cleaning the sleeves. Also, the time since the last sleeve cleaning can be incorporated and the fouling factor can be tracked over time to determine the rate of fouling and the cost implications of this continued fouling. Comparing these costs to the cost of cleaning the sleeves (which is dependent on the system design) can allow a decision to be made about when to clean the sleeves.

Embodiments of the present invention will be described with reference to the following Example which should not be used to construe or limit the scope of the present invention.

EXAMPLE

A groundwater sample contaminated with trichloroethylene (TCE) was treated using a bench-scale recirculating batch photoreactor. The semi-batch UV reactor consists of a 32 L reservoir, a 6 L UV chamber housing a 12.4 watt low-pressure lamp and a recycle pump that draws the solution from the reservoir and pumps it to the UV chamber and back to the reservoir at a controlled flow rate of 110 liters per minute. A water-cooling jacket was mounted on the re-circulation pipe to maintain a constant temperature during the irradiation. The unit was provided with a sampling port, which allowed sampling of the solution at specific UV exposure times.

The test procedure comprised rinsing the apparatus with tap water and allowing it to completely drain, transferring 25 liters of the groundwater sample into the reservoir, adding the required amounts of hydrogen peroxide and TCE with the recirculation pump on, collecting the initial (t=0) sample, turning on the UV lamp and collecting subsequent water samples as required.

Forty milliliter samples were collected for TCE analysis in sample vials provided by the analytical laboratory (i.e., Maxxam Analytics Inc.). Additional samples were collected for the determination of hydrogen peroxide concentrations and UV absorbance.

The results of this treatment study are presented in Table 4. Although both the TCE (i.e., contaminant) and the hydrogen peroxide concentrations have been measured, the data provides an example to illustrate the capability of the described model to predict the TCE conversion based on the measured change in hydrogen peroxide concentration. The relevant kinetic parameters that are required for this prediction are:

$$k_{TCE,OH} = 2.9 \times 10^9 \text{ M}^{-1}\text{s}^{-1};$$

$$k_{H2O2,OH} = 2.7 \times 10^7 \text{ M}^{-1}\text{s}^{-1};$$

$$\sum_i k_{s_i,OH}[S_i]_o = 1.8 \times 10^5 \text{ s}^{-1}$$

and an example calculation using equation 13 is given as:

$$\text{Log}(TCE_0/TCE) = \frac{0.98 \times 2 \times 2.9 \times 10^9}{34{,}000 \times \text{Ln}(10) \times \left(2.7 \times 10^7 \times \frac{(5.33+4.36)}{2 \times 34{,}000} + 1.81 \times 10^5\right)} = 0.39 \quad (25)$$

where the initial and final hydrogen peroxide concentrations are 5.33 and 4.36 ppm respectively. The EE/O associated with this log reduction is:

$$EE/O = \frac{0.0124 \text{ kW} \times 60 \text{ min} \times 3785 \text{ L/kgal}}{60 \text{ min/h} \times 24.79 \text{ L} \times 0.39 \text{ orders}} = 4.85 \text{ kWh/kgal/order} \quad (26)$$

Figure 9:
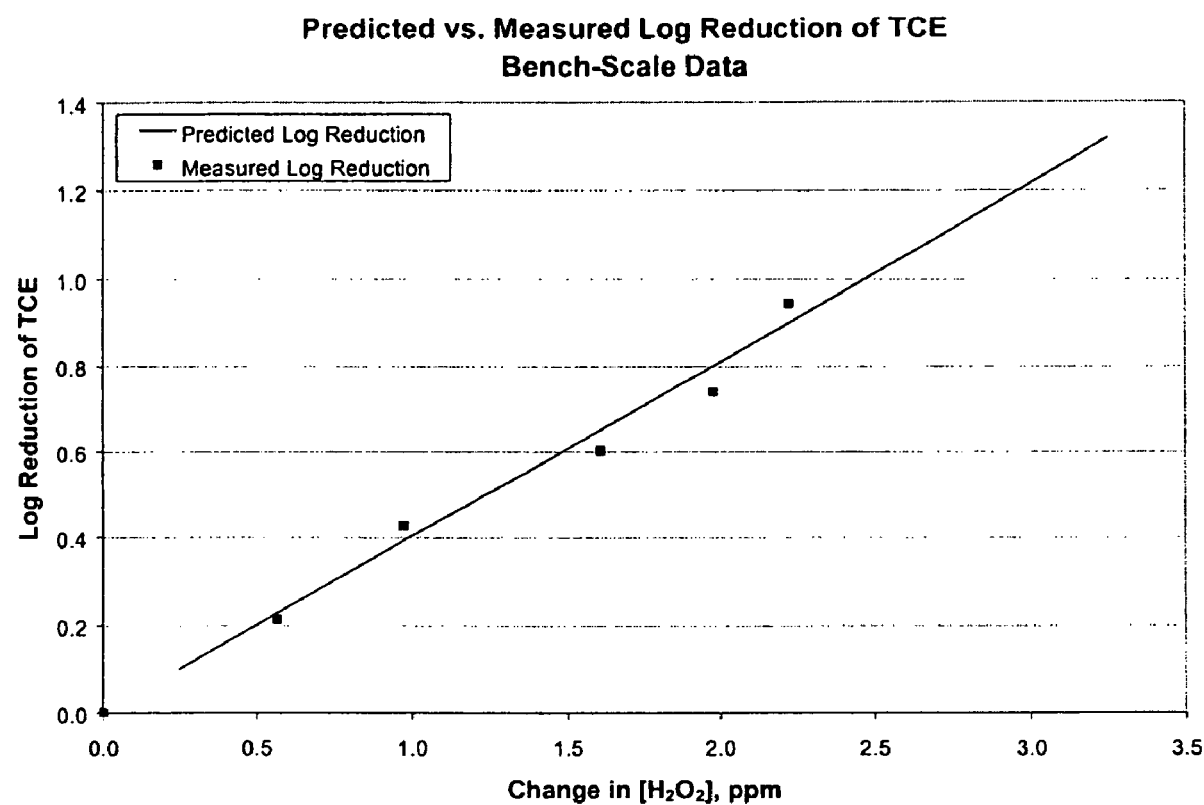
FIGS. 9-10 each illustrate graphical data referred to in the Example below.

Table 4 presents both the predicted log reduction of TCE and the associated $E_{EO}$ values based on the model and the measured reduction in peroxide concentration. A comparison of the predicted Log reduction values with the measured values is shown in FIG. 9.

TABLE 4

UV Photooxidation of TCE Contaminated Groundwater

| | Peroxide Concentration | | [TCE] | | | | |
| --- | --- | --- | --- | --- | --- | --- | --- |
| | | | | Measured | | Predicted | |
| Time (min) | [$H_2O_2$], (ppm) | Δ[$H_2O_2$], ppm | (ppb) | Log ($C_0/C_t$) | EE/O, (kWh/kgal/order) | Log ($C_0/C_t$) | EE/O, (kWh/kgal/order) |
| 0 | 5.33 | 0.00 | 88 | 0.000 | N/A | 0.000 | N/A |
| 30 | 4.76 | 0.57 | 54 | 0.212 | 4.46 | 0.228 | 4.13 |
| 60 | 4.36 | 0.98 | 33 | 0.426 | 4.44 | 0.391 | 4.84 |
| 90 | 3.72 | 1.61 | 22 | 0.602 | 4.72 | 0.646 | 4.47 |

TABLE 4-continued

UV Photooxidation of TCE Contaminated Groundwater

| | Peroxide Concentration | | [TCE] | | | |
|---|---|---|---|---|---|---|
| | | | Measured | | Predicted | |
| Time (min) | $[H_2O_2]$, (ppm) | $\Delta[H_2O_2]$, ppm | (ppb) | Log $(C_0/C_t)$ | EE/O, (kWh/kgal/order) | Log $(C_0/C_t)$ | EE/O, (kWh/kgal/order) |
| 120 | 3.35 | 1.98 | 16 | 0.740 | 5.11 | 0.796 | 4.97 |
| 150 | 3.10 | 2.23 | 10 | 0.944 | 5.01 | 0.895 | 5.69 |

Figure 10:
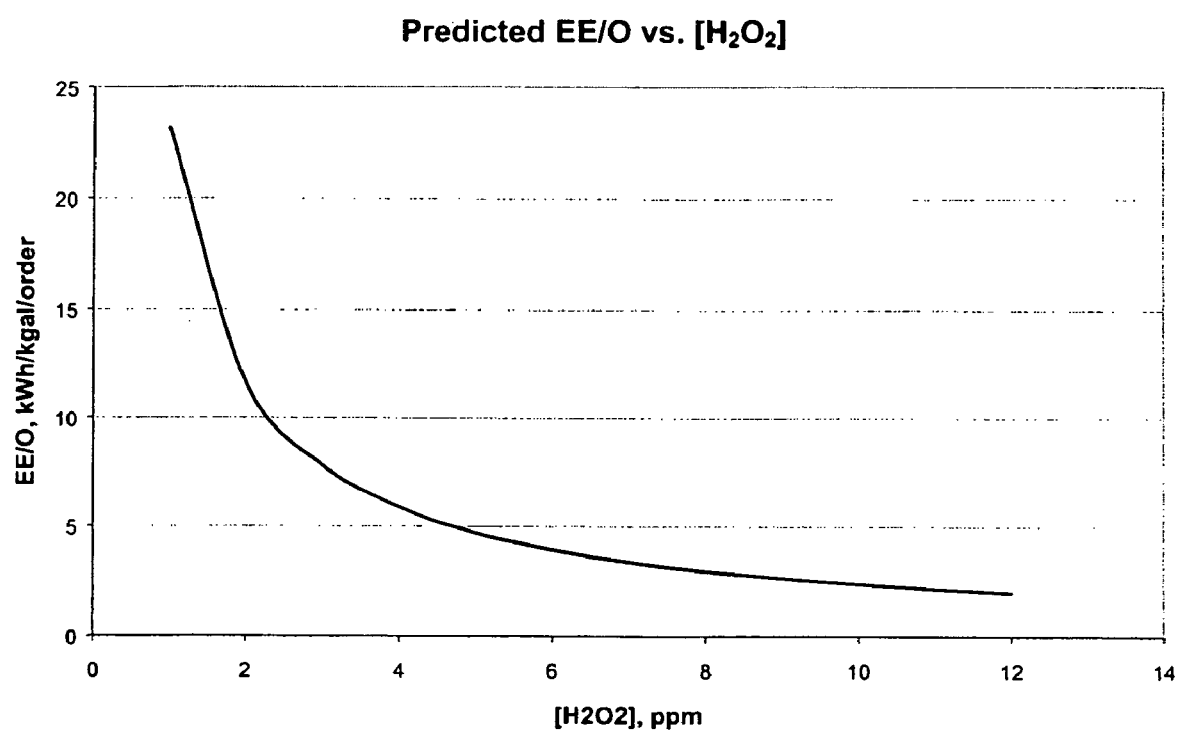

Since the initial hydrogen peroxide concentration is 5.33 ppm, then the ratio of $\Delta[H_2O_2]$ to $[H_2O_2]$ can be substituted into equation 20 resulting in the following $E_{EO}$ vs. $[H_2O_2]$ correlation, which is illustrated graphically in FIG. 10.

$$E_{EO} = \frac{4.36(2.7 \times 10^7 [H_2O_2]_0 + 1.81 \times 10^5)}{1.07 \times 10^9 [H_2O_2]_0} \qquad (27)$$

Since the power required to maintain system performance is linked to the $E_{EO}$ and the $E_{EO}$ is correlated with hydrogen peroxide concentration, then the required system power can be correlated with hydrogen peroxide concentration. The total O&M costs can be correlated with the concentration of hydrogen peroxide and this correlation can be solved for the hydrogen peroxide concentration that results in the minimum system operating cost. Once this concentration is known the corresponding system power can also be calculated. Thus, the optimum system power and hydrogen peroxide concentration are both determined.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. An ultraviolet fluid treatment system for treating a fluid containing a contaminant, the system comprising:
    a fluid inlet, a fluid outlet, and an ultraviolet radiation zone between the fluid inlet and the fluid outlet;
    an upstream measurement point configured to measure a first set of fluid properties upstream of the radiation zone;
    a downstream measurement point configured to measure a second set of fluid properties downstream of the radiation zone;
    a controller configured to cause one or more fluid treatment system parameters to be adjusted; and
    a programmable logic device programmed with a kinetic calculation model that outputs a conversion value of the contaminant based on the first and second sets of fluid properties, said programmable logic device also programmed with a reactor calculation model that calculates an adjustment to the one or more of the fluid treatment system parameters based on the output conversion value, the programmable logic device outputting the calculated adjustment parameters to the controller, which in response thereto adjusts the one or more fluid treatment system parameters.

2. The ultraviolet fluid treatment system of claim 1, wherein the contaminant comprises one or more chemical compounds, one or more microorganisms, or a combination thereof.

3. The ultraviolet fluid treatment system of claim 1, wherein the first set, the second set, or the first and second sets of fluid properties comprise:
    rate of fluid flow;
    ultraviolet light transmittance of the fluid;
    pH of the fluid;
    conductivity of the fluid;
    total organic carbon (TOC) concentration of the fluid;
    concentration of solids in the fluid;
    concentration of an oxidant;
    concentration of an actinometer;
    temperature of the fluid,
    particle size analysis; or
    any combination thereof.

4. The ultraviolet fluid treatment system of claim 3, wherein the first and the second sets of fluid properties comprise the concentration of an oxidant.

5. The ultraviolet fluid treatment system of claim 4, wherein the oxidant comprises hydrogen peroxide, ozone, or a combination thereof.

6. The ultraviolet fluid treatment system of claim 3, wherein the first and the second sets of fluid properties comprise the concentration of an actinometer.

7. The ultraviolet fluid treatment system of claim 6, wherein the actinometer comprises uridine, hydrogen peroxide, or potassium iodide/iodate.

8. The ultraviolet fluid treatment system of claim 1, wherein the fluid treatment system comprises one or more ultraviolet lamps for providing ultraviolet radiation to the radiation zone, and wherein the fluid treatment system parameters comprise:
    power incident to the system;
    a power setting of the system;
    rate of fluid flow through the system;
    rate of addition of an oxidant to the system; or,
    any combination thereof.

9. The ultraviolet fluid treatment system of claim 8, wherein the fluid treatment system parameters comprise the rate of addition of an oxidant to the system.

10. The ultraviolet fluid treatment system of claim 9, wherein the oxidant comprises hydrogen peroxide, ozone, or a combination thereof.

11. A control center for an ultraviolet fluid treatment system for treating a fluid containing a contaminant, the control center comprising:
a controller configured to adjust one or more fluid treatment system parameters; and,
a programmable logic device programmed with a kinetic calculation model that calculates and outputs a conversion value of the contaminant, said programmable logic device also programmed with a reactor calculation model that calculates and outputs an adjustment to the one or more fluid treatment system parameters based on the output conversion value, the programmable logic device outputting the calculated adjustment parameters to the controller, which in response thereto adjusts the one or more fluid treatment system parameters.

12. The control center of claim 11, wherein the controller and the programmable logic device are located within a control center enclosure.

13. The control center of claim 11, wherein the controller and the programmable logic device are co-located.

14. The control center of claim 11, wherein the control center comprises an operator interface in communication with the controllers, and wherein the operator interface is configured to manually adjust one or more fluid treatment system parameters using the controller.

15. An ultraviolet fluid treatment apparatus comprising:
a fluid inlet, a fluid outlet, and an ultraviolet radiation zone between the fluid inlet and the fluid outlet; and,
a control center according to claim 11.

16. The ultraviolet fluid treatment apparatus of claim 15, wherein the control center is located remotely from the ultraviolet fluid treatment apparatus and is in communication with the ultraviolet fluid treatment apparatus.

17. The ultraviolet fluid treatment apparatus of claim 15, wherein the apparatus comprises an oxidant injector upstream of the ultraviolet radiation zone.

18. The ultraviolet fluid treatment apparatus of claim 15, wherein the apparatus comprises structure configured to cause fluid mixing.

19. An ultraviolet fluid treatment system for treating a fluid containing a contaminant, the system comprising:
a fluid inlet, a fluid outlet, an ultraviolet radiation zone between the fluid inlet and the fluid outlet, and an oxidant injection site upstream of the radiation zone, the oxidant injection site configured to inject an oxidant into the fluid;
an upstream measurement point configured to measure a first set of fluid properties upstream of the radiation zone, the first set of fluid properties including a first concentration of the oxidant;
a downstream measurement point configured to measure a second set of fluid properties downstream of the radiation zone, the second set of fluid properties including a second concentration of the oxidant;
a controller configured to cause one or more fluid treatment system parameters to be adjusted; and
a programmable logic device programmed with a kinetic calculation model that calculates and outputs a conversion value of the contaminant based on a difference between the first concentration of oxidant and the second concentration of oxidant, said programmable logic device also programmed with a reactor calculation model that calculates and outputs an adjustment to the one or more fluid treatment system parameters based on the calculated and output conversion value, the programmable logic device outputting the calculated adjustment parameters to the controller.

20. The ultraviolet fluid treatment system of claim 19, wherein the oxidant comprises hydrogen peroxide, ozone, or a combination thereof.

21. The ultraviolet fluid treatment system of claim 19, wherein the contaminant comprises one or more photo-oxidizable or photo-lyzable chemical compounds selected from the group consisting of:
aromatic hydrocarbons;
chlorinated organic hydrocarbons;
nitrogen containing organic compounds;
ethers; and,
any combination thereof.

22. A system for predicting the reduction in concentration of a target material to a predetermined concentration in a flow of fluid passing through a fluid treatment zone in a fluid treatment device, the flow fluid comprising a marker compound, the system comprising:
a first measurement device configured to obtain a first measurement comprising the concentration of the marker compound in the flow of fluid at a first location upstream of the fluid treatment zone;
a second measurement device configured to obtain a second measurement comprising the concentration of the marker compound in the flow of fluid at a second location, the second location being downstream with respect to the first location; and
processing structure configured to (i) correlate the first measurement and the second measurement to a calculated concentration of the target material, (ii) compare the calculated concentration with the predetermined concentrations, and (iii) adjust at least one process parameter if the calculated concentration is different than the predetermined concentration.

23. The system defined in claim 22, wherein the flow of fluid comprises water.

24. The system defined in any one of claims 22-23, wherein the first location is disposed upstream of the fluid treatment zone.

25. The system defined in any one of claims 22-23, wherein the second location is disposed downstream of the fluid treatment zone.

26. The system defined in any one of claims 22-23, wherein the first location is disposed upstream of the fluid treatment zone and the second location is disposed downstream of the fluid treatment zone.

27. The system defined in any one of claims 22-23, wherein the fluid treatment zone comprises at least one radiation source.

28. The system defined in any one of claims 22-23, wherein the fluid treatment zone comprises at least one radiation source.

29. The system defined in any one of claims 22-23, wherein the fluid treatment zone comprises at least one ultraviolet radiation source.

30. The system defined in any one of claims 22-23, wherein the fluid treatment zone comprises an array of radiation sources.

31. The system defined in any one of claims 22-23, wherein the fluid treatment zone comprises an array of ultraviolet radiation sources.

32. The system defined in any one of claims 22-23, wherein the target material comprises a contaminant.

33. The system defined in claim 32, wherein the contaminant is selected from the group comprising a chemical compound, a microorganisms, and mixtures thereof.

34. The system defined in any one of claims 22-23, wherein the marker compound comprises a reactant compound which will cause the reduction in the concentration of the target material.

35. The system defined in claim 34, wherein the reactant compound comprises an oxidant.

36. The system defined in claim 34, wherein the reactant compound comprises a peroxide, ozone and mixtures thereof.

37. The system defined in claim 22-23, wherein the marker compound comprises an actinometer.

38. The system defined in any one of claims 22-23, wherein the at least one process parameter is selected from one or more of: an amount of power incident to the system; a power setting at which the system is operated; a rate of fluid flow through the system; a rate of addition of an oxidant to the system; and any combination thereof.

39. The system defined in any one of claims 22-23, wherein the processing structure comprises a programmable logic controller.

40. The system defined in any one of claims 22-23, wherein the processing structure comprises a programmable logic controller that is programmed with a reactor calculation model.

41. The system defined in any one of claims 22-23, wherein the processing structure comprises a programmable logic controller that is programmed with a kinetic model of the fluid treatment zone.

42. The system defined in any one of claims 22-23, wherein the processing structure comprises a programmable logic controller that is programmed with a reactor model including the fluid treatment zone.

43. A system for predicting the reduction in concentration of a target contaminant to a predetermined concentration in a flow of water passing through an ultraviolet radiation treatment zone comprising an array of ultraviolet radiation sources, the flow of water comprising an oxidant, the system comprising:
- a first measurement-device configured to obtain a first concentration of the oxidant in the flow of water at a first location upstream of the ultraviolet radiation treatment zone;
- a second measurement device configured to obtain a second concentration of the oxidant in the flow of water at a second location, the second location being downstream with respect to the first location; and
- logic structure configured to (i) correlate the first concentration and the second concentration to a calculated concentration of the target contaminant, (ii) compare the calculated concentration with the predetermined concentrations, and (iii) adjust at least one process parameter if the calculated concentration different than the predetermined concentration.

44. The system defined in claim 43, wherein the oxidant is selected from hydrogen peroxide, ozone and mixtures thereof.

45. The system defined in any one of claims 43-44, wherein the target contaminant comprises a chemical compound.

46. The system defined in any one of claims 43-44, wherein the target contaminant comprises a microorganism.

47. The system defined in any one of claims 43-44, wherein the at least one process parameter comprises at least one of: (i) an amount of oxidant added to the flow water upstream of ultraviolet radiation treatment zone, and (ii) an amount of power supplied to the ultraviolet radiation sources, and (iii) supply of power to a portion of the ultraviolet radiation sources.

* * * * *